US010178976B2

United States Patent
Liu et al.

(10) Patent No.: US 10,178,976 B2
(45) Date of Patent: Jan. 15, 2019

(54) METHOD AND APPARATUS FOR TEMPERATURE CONTROL IN A PET DETECTOR

(71) Applicant: SHANGHAI UNITED IMAGING HEALTHCARE CO., LTD., Shanghai (CN)

(72) Inventors: Weiping Liu, Shanghai (CN); Yixing Sun, Shanghai (CN); Lingzhi Hu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 176 days.

(21) Appl. No.: 15/101,494

(22) PCT Filed: Jan. 29, 2016

(86) PCT No.: PCT/CN2016/072696
§ 371 (c)(1),
(2) Date: Jun. 3, 2016

(87) PCT Pub. No.: WO2017/128281
PCT Pub. Date: Aug. 3, 2017

(65) Prior Publication Data
US 2018/0035957 A1 Feb. 8, 2018

(51) Int. Cl.
*G01T 1/164* (2006.01)
*A61B 6/03* (2006.01)
(Continued)

(52) U.S. Cl.
CPC .............. *A61B 6/035* (2013.01); *A61B 5/055* (2013.01); *A61B 6/037* (2013.01); *A61B 6/4417* (2013.01);
(Continued)

(58) Field of Classification Search
CPC ... G01T 1/2985; G01T 1/1642; G01T 1/1644; G01T 1/202; G01T 1/172
See application file for complete search history.

(56) References Cited

U.S. PATENT DOCUMENTS

| 3,368,614 | A | 2/1968 | Anderson |
| 8,481,949 | B2 | 7/2013 | Martin |

(Continued)

FOREIGN PATENT DOCUMENTS

| CN | 201274634 Y | 7/2009 |
| WO | 2015189786 A1 | 12/2015 |

OTHER PUBLICATIONS

International Search Report in PCT/CN2016/072696 dated Oct. 31, 2016, 5 pages.
(Continued)

*Primary Examiner* — David Porta
*Assistant Examiner* — Mamadou Faye
(74) *Attorney, Agent, or Firm* — Metis IP LLC

(57) ABSTRACT

The present disclosure relates to a PET detector module suitable for using in a PET/MR hybrid system. The PET detector module comprises a scintillator, a set of frontend electronics and a positioning means configured to securing relative position between the scintillator and the frontend electronics. The PET detector module may further comprise a temperature control system, such as an air-cooling system or a heat exchange plate. The present disclosure also relates to a heat exchange plate, which comprises a fluidic passage for containing a flow of a heat exchange media. The heat exchange plate is suitable for use in the magnetic field environment of a MRI system.

20 Claims, 14 Drawing Sheets

(51) Int. Cl.
*A61B 6/00* (2006.01)
*A61B 5/055* (2006.01)
*G01T 1/29* (2006.01)
*G06T 7/00* (2017.01)

(52) U.S. Cl.
CPC .......... *G01T 1/1642* (2013.01); *G01T 1/2985* (2013.01); *G06T 7/0012* (2013.01); *A61B 6/5235* (2013.01); *G06T 2207/10081* (2013.01); *G06T 2207/10088* (2013.01)

(56) References Cited

U.S. PATENT DOCUMENTS

| | | | |
|---|---|---|---|
| 2004/0218167 A1* | 11/2004 | Johan Hol | G03F 7/70758 355/72 |
| 2010/0243908 A1* | 9/2010 | Shoji | G01T 1/2002 250/370.11 |
| 2012/0091341 A1 | 4/2012 | Corbeil et al. | |
| 2013/0284936 A1* | 10/2013 | McBroom | G01R 33/481 250/363.03 |
| 2014/0312718 A1 | 10/2014 | Li et al. | |
| 2014/0361181 A1 | 12/2014 | Liu | |

OTHER PUBLICATIONS

Written Opinion in PCT/CN2016/072696 dated Oct. 31, 2016, 4 pages.
Partial Search Report in European Application No. 16815530.7 dated Oct. 22, 2018, 10 pages.

* cited by examiner

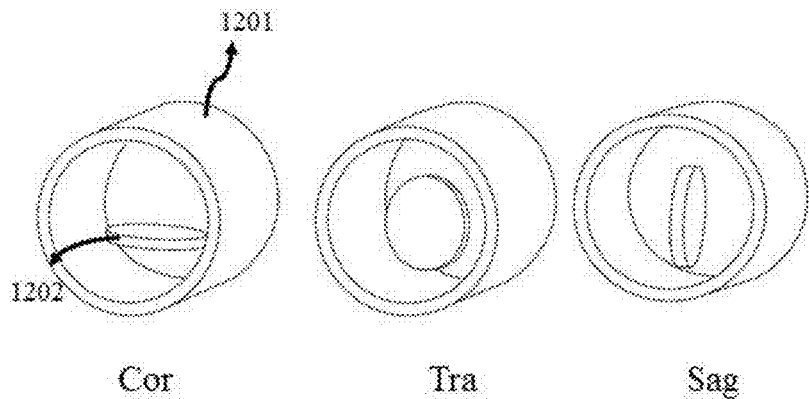
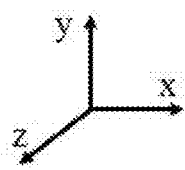
FIG. 12A
| Cor-z | Cor-x | Cor-y |
| --- | --- | --- |
| Sag-z | Sag-x | Sag-y |
| Tra-z | Tra-x | Tra-y |
FIG. 12B

|  |  | Without cold plates | With cold plates | Rate (%) |
|---|---|---|---|---|
| Homogeneity of B0 | A00 (Hz) | 128132298 | 128132280 | -0.00001405 |
|  | A10 (mT/m) | 1.0161 | 1.0171 | 0.098416 |
|  | B11 (mT/m) | -1.2506 | -1.2506 | 0 |
|  | A11 (mT/m) | -0.061 | -0.061 | 0 |
|  | A20 (mA) | -93 | -104 | 11.828 |
|  | A21 (mA) | -64 | -63 | -1.5625 |
|  | B21 (mA) | -7 | 0 | -100 |
|  | A22 (mA) | 41 | 44 | 7.3171 |
|  | B22 (mA) | -115 | -113 | -1.739 |
| Transmit reference voltage | Transmitter Voltage | 233.4433 | 251.1355 | 7.577942909 |

FIG. 14

METHOD AND APPARATUS FOR TEMPERATURE CONTROL IN A PET DETECTOR

CROSS-REFERENCE TO RELATED APPLICATIONS

The present application is a U.S. National Stage entry under 35 U.S.C. § 371 of International Application No. PCT/CN2016/072696, filed on Jan. 29, 2016, designating the United States of America, the contents of which are hereby incorporated by reference.

TECHNICAL FIELD

This application relates to multi-modality imaging technology, including positron emission tomography (PET) and magnetic resonance (MR) hybrid imaging systems. Particularly, this application relates to PET components that are suitable for working under magnetic fields applied by a PET/MR hybrid system. More particularly, this application relates to apparatus for controlling the working temperature of PET components in a PET/MR hybrid system.

BACKGROUND

Positron emission tomography (PET) is a specialized radiology procedure that generates and examines three-dimensional images of functional processes in a target organ or tissue of a body. Specifically, in PET studies, a biologically active molecule carrying a radioactive tracer is first introduced to a patient's body. The PET system then detects gamma rays emitted by the tracer and constructs a three-dimensional image of the tracer concentration within the body by analyzing the detected signal. Because the biologically active molecules used in PET studies are natural substrates of metabolism at the target organ or tissue, PET can evaluate the physiology (functionality) and anatomy (structure) of the target organ or tissue, as well as its biochemical properties. Changes in these properties of the target organ or tissue may provide essential information for the identification of the onset of a disease process before any anatomical changes related to the disease become detectable by other diagnostic tests, such as computed tomography (CT) or magnetic resonance imaging (MRI).

Furthermore, the unique high sensitivity of PET—in the picomolar range—allows detection of even minute amounts of radio-labeled markers in vivo, making PET the modality of choice for molecular imaging. In this respect, an important new perspective in the field of nuclear imaging was created by using PET in conjunction with other diagnostic tests to realize simultaneous acquisition of both structural and functional information of the body and provide more definitive information about malignant (cancerous) tumors and other lesions. For example, since the introduction of combined PET/CT (computed tomography) systems about 10 years ago, medical practitioners in the fields of oncology, neurology, cardiology and radiology have been taken advantages of the dual-modality system to construct and analyze three-dimensional functional PET images in comparison with structural x-ray CT images that are obtained almost simultaneously with a same PET/CT scanner in a single session.

To this end, there are many clinical indications where magnetic resonance imaging (MRI) is preferred over CT. For example, MRI offers, compared to CT, better soft tissue contrast and does not use ionizing radiation, thus significantly reducing the overall required radiation doses and associated risk or harm to a patient. Furthermore, in addition to structural imaging, MRI can also be used to visualize functional activity of the body. For example, functional MRI or fMRT, measures changes in blood flow to different parts of the brain. In this type of studies, signals reflecting the blood-oxygen levels in the brain can be reliably used as a proxy for brain activity, because neurons use more oxygen when they are active.

Thus, the current need in the field of non-invasive diagnostic imaging to accurately and transparently combine high resolution, three-dimensional functional PET information with equally high quality morphological and/or functional MRI information within a single device establishes a clear new direction for research and development of next generation multi-modality imaging technology.

A PET/MR hybrid system capable of simultaneous dual-modality imaging would provide many advantages which go far beyond simply combining separately acquired PET and MRI data. These advantages include not only great convenience, flexibility, and improved speed for multi-modality acquisition of more data, but also much simplified logistics of patient management and significantly reduced patient costs. More importantly, simultaneous multi-modality data acquisition and processing ensure far greater accuracy in registration of PET and MRI data, hence providing medical practitioners more detailed and reliable diagnostic information.

However, despite great endeavor in the field, several technical difficulties continue to exist and hinder the realization of full PET/MR integration and real simultaneous data acquisition. Particularly, PET and MRI are two advanced imaging technologies, which require collecting and processing electronic signals that are delicate and prone to interference. For example, a PET detector may contain temperature-sensitive components and thus need a cooling apparatus to maintain a suitable working temperature. Additionally, optimal functionality of a PET detector also relies on precise coupling and communication between its optical and electrical components. Thus, a PET detector may also contain various mechanical parts to hold the components in precise positions relative to one another. However, the cooling apparatus and/or mechanical parts of a PET detector, when placed into a MRI gantry, may significantly disturb homogeneity of the MRI magnetic field. Further, another major challenge exists with the physical constrains on available space when trying to integrate various PET components into a MM system.

Thus, there exists a need in the field to provide an improved PET detector that overcomes the technical challenges mentioned above.

SUMMARY

In a first aspect of the present disclosure, provided herein is a PET detector module. In some embodiments, the PET detector module may include a scintillator, a set of frontend electronics, and a positioning means. The positioning means may exert a compressive force that presses the set of frontend electronics against the scintillator, thus secure relative position between the scintillator and the set of frontend electronics. In some embodiments, the positioning means may comprise a compressive layer having a compressive surface, and the compressive layer may extend the compressive surface towards the set of frontend electronics and the compressive surface may press the set of frontend electronics against the scintillator. In some embodiments, the set of frontend electronics may have a larger area than the compressive surface, or the set of frontend electronics may have a same area as the compressive surface. The compressive surface may be continuous or discontinuous. The compressive force may be uniform or non-uniform across the compressive surface. In some embodiments, the PET detector module may further comprise a temperature control means for controlling temperature at one or more target locations of the PET detector module. In some embodiments, the temperature control means may establish at least one fluidic passage near the one or more target locations, and the fluidic passage may contain a flow of a heat exchange media. In some embodiments, the heat exchange media is gaseous, liquid or solid. In some embodiments, the temperature control means may comprise a plate having two opposing ends. In some embodiments, the plate may comprise one or more partial slots each having a pair of open and closed ends and the pair of open and closed ends may locate at the opposing ends of the plate. In some embodiments, the plate may further comprise one or more complete slots each having a pair of open ends and the pair of open ends locate at the opposing ends of the plate. In some embodiments, the fluidic passage is a tubing embedded within the plate or a channel internal to the plate. The fluidic passage may be alongside one or more of the partial and complete slots. In some embodiments, the plate may be made of an electrical conductive material, and one or more of the partial and complete slots may be filled with an electrical insulating material. In some embodiments, the set of frontend electronics and the plate may sandwich the compressive layer, and the compressive layer may be thermal conductive. In some embodiments, the plate and the set of readout electronics may sandwich the thermal conductive layer. In some embodiments, the thermal conductive layer may be compressive. In some embodiments, the temperature control means may comprise an air passage near the set of frontend electronics.

In a second aspect of the present disclosure, provided herein is a PET detector module, and the PET detector module may comprise a scintillator, a set of frontend electronics, a first thermal conductive layer, a heat exchange plate, a second thermal conductive layer and a set of readout electronics. The set of frontend electronics may attach the scintillator. The set of frontend electronics may attach the scintillator. The first and second thermal conductive layers may sandwich the heat exchange plate. The first thermal conductive layer may attach the set of frontend electronics. The second thermal conductive layer attaches the set of readout electronics. At least one of the first and second thermal conductive layer exerts a compressive force towards the set of frontend electronics; and the compressive force secures relative position between the set of frontend electronics and the scintillator.

In a third aspect of the present disclosure, provided herein is a PET detector module, and the PET detector module may comprise a scintillator, a set of frontend electronics, a set of springs, a supportive frame, a set of readout electronics, and an air box. The set of frontend electronics may attach the scintillator. The supportive frame may have a first side and a second side, and the first side and the set of frontend electronics may form a first cavity in between, the second side and the air box may form a second cavity, the first and second cavities may be in fluidic communication. The set of springs may locate in the first cavity, the set of springs may exert a compressive force towards the set of frontend electronics, and the compressive force may secure relative position between the set of frontend electronics and the scintillator. The set of readout electronics may locate in the second cavity. The first and second cavities form an air passage near the set of frontend electronics and the set of readout electronics.

In a fourth aspect of the present disclosure, provided herein is a heat exchange plate, and the heat exchange plate may comprise a fluidic passage and a plate having two opposing ends. The fluidic passage may contain a flow of a heat exchange media. The plate may comprise a plurality of partial slots each having a pair of open and closed ends. The pair of open and closed ends may locate at the opposing ends of the plate. The open ends of two adjacent partial slots may locate at the opposing ends of the plate. The fluidic passage may be alongside each partial slot, wherein the fluidic passage may turn 180 degrees around each close end. The fluidic passage may be a tubing embedded within the plate, or it may be a channel internal to the plate. In some embodiments, the fluidic passage may be a tubing having a first portion, a second portion and a third portion, wherein the first and second potions may be embedded within the plate, the first and second portions being alongside at least one of the partial slots, and the third portion is external to the plate, connecting the first and second portions into fluidic communication.

In a fifth aspect of the present disclosure, provided herein is a heat exchange plate, and the heat exchange plate may comprise a fluidic passage and a plate having two opposing ends. The fluidic passage may contain a flow of a heat exchange media. The plate may comprise a plurality of partial slots each having a pair of open and closed ends. The pair of open and closed ends may locate at the opposing ends of the plate. The open ends of two adjacent partial slots may locate at a same end of the two opposing ends of the plate. In some embodiments, the fluidic passage may be alongside at least one partial slot, and the fluidic passage may turn 180 degree around at least one closed end. In some embodiments, the fluidic passage may be a tubing embedded within the plate, and in some embodiments, the fluidic passage may be a channel internal to the plate. In some embodiments, the plate may be made of an electrical conductive material and one or more of the partial slots may be filled with an electrical insulating material.

In a sixth aspect of the present disclosure, provided herein is a heat exchange plate, and the heat exchange plate may have two opposing ends and a fluidic tubing configured to contain a flow of a heat exchange media. The plate may comprise a plurality of complete slots each having a pair of open ends, the pair of open ends locating at the opposing ends of the plate, and the complete slots dividing the plate into a plurality of segments. The fluidic tubing may comprise a plurality of embedded portions and a plurality of unembedded portions, wherein each embedded portion is embedded within one of the plurality of segments. And each unembedded portion may connect two of the plurality of embedded portions into fluidic communication. In some embodiments, the heat exchange plate may be made of an electrical conductive material and one or more of the complete slots may be filled with an electrical insulating material.

BRIEF DESCRIPTION OF THE DRAWINGS

The present disclosure is further described in terms of exemplary embodiments. These exemplary embodiments are described in detail with reference to the drawings. These embodiments are non-limiting examples, in which like reference numerals represent similar structures throughout the several views of the drawings, and wherein:

FIG. 9A is a schematic drawing illustrating a perspective view and FIG. 9B is a schematic drawing illustrating a cross-section view of the PET detector module;

FIGS. 12A and 12B illustrate a method of evaluating the effect of the heat exchange plate on the imaging modality of the imaging system according to some embodiments of the present disclosure;

FIG. 14 illustrate another exemplary test results for the effect of the heat exchange plate on the imaging modality of the imaging system according to some embodiments of the present disclosure;

DETAILED DESCRIPTION

Figure 1:
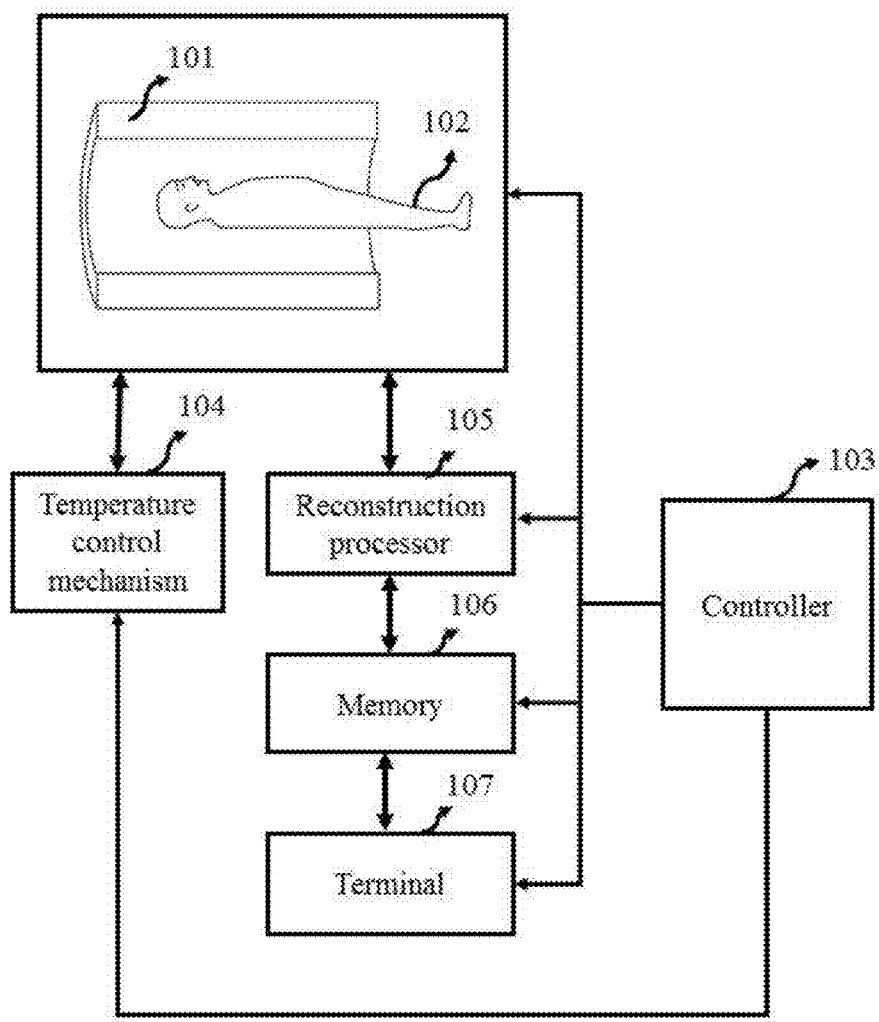
FIG. 1 is a schematic illustration of an imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to" or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive biomedical imaging, such as for disease diagnostic or research purposes. The system may comprise a single imaging modality or multiple imaging modalities for conducting different medical scans or studies, including but not limited to ultrasound scan, X-ray scan, bone densitometry, fluoroscopy, computed tomography (CT), Digital Radiography (DR), Single Photon Emission Computed Tomography (SPECT), magnetic resonance imaging (MRI) and positron emission tomography (PET).

The term "imaging modality" or "modality" as used herein broadly refers to an imaging method or technology that gathers, generates, processes and/or analyzes imaging information of a target body through a particular mechanism. The term "target body" as used herein broadly relates to any organic or inorganic mass, natural or man-made, that has a chemical, biochemical, biological, physiological, biophysical and/or physical activity or function. Exemplary embodiments of a target body pertaining to the present disclosure include cells, tissues, organs or whole bodies of human or animal. Other exemplary embodiments include but not limited to man-made composition of organic and/or inorganic matters that are with or without life.

Accordingly, a multi-modality imaging system of the present disclosure can include more than one imaging modality, such as two, three, or more different modalities. In a multi-modality system, the mechanisms through which different imaging modalities operate or function can be the same or different. Accordingly, the imaging information can also be the same or different. For example, in some embodiments, the imaging information can be internal and/or external information, and can be functional and/or structural information of the target body. Particularly, in some embodiments, the imaging information of different modalities complement one another, thereby providing a set of imaging data describing a target body from different analytical angles. For example, in some embodiments, the multi-modality imaging achieves merging of morphological and functional images.

For example, in some embodiments, the multi-modality system includes a computed tomography (CT) imaging modality, which is a medical imaging method that combines multiple X-ray projections taken from different angles to produce detailed cross-sectional images of internal areas of the target body. Thus, CT imaging information offers medical practitioners precise, three-dimensional views of certain internal parts of the target body, such as soft tissues, bones, blood vessels, important organs of a human body, without performing invasive procedures on the target body. In some embodiments, the multi-modality system includes an ultrasound imaging modality, which is a medical imaging technology that uses high frequency sound waves to create images of the internal of the target body. Particularly, in some embodiments, the ultrasound imaging modality sends sound waves into the body and is able to convert the returning sound echoes into an image. In some embodiments, an ultrasound imaging modality can be used to diagnose abnormalities in the heart and blood vessels and assess conditions of pregnancy, health of organs in the pelvis and abdomen, or symptoms of pain, swelling and infection of a human subject. In some embodiments, the multi-modality system includes an X-ray imaging modality, which is an imaging technology that uses ionizing radiation to produce images of a target body's internal structure by sending X-ray beams through the target body, which are absorbed in different amounts depending on the density of the material.

In some embodiments of the present disclosure, the multi-modality imaging system comprises imaging modules and components for conducting MR imaging and analysis. MRI is a non-invasive imaging technique that uses a powerful magnet to align the nuclei of atoms inside a target body, and a variable magnetic field that causes the atoms to resonate, a phenomenon called nuclear magnetic resonance. The nuclei produce their own rotating magnetic fields that a scanner detects and uses to create an image of internal of the target body.

Specifically, a MRI scanner typically includes three main parts, namely a system that generates a static homogenous magnetic field, sometimes referred to as the main magnetic field; a system that generates and receives radiofrequency (RF) radiation; and a system that generates a magnetic gradient field, i.e., a magnetic field with varying strength along one direction.

Particularly, when the MRI scanner applies the strong magnetic field to a target body, the applied field has a tendency to align magnetic moments (spins) of nuclei in the target body along the magnetic field. Many atomic nuclei of interest in MRI studies have their characteristic resonant frequencies in the RF range of the electromagnetic spectrum. Thus, after the main magnetic field has been applied to align the nuclei in the target body, the MRI scanner produces a RF current that creates an oscillating electromagnetic field. When the frequency of the oscillating electromagnetic field matches the characteristic resonant frequency of the aligned nuclei, the aligned nuclei absorb the energy of the oscillation electromagnetic field and flip their spins. Subsequently, the RF electromagnetic field is turned off, and the nuclei gradually return to their original spin in a process known as precession or relaxation. The return process produces the nuclear magnetic resonance (NMR) signal, which leaves the target body as RF electromagnetic radiation and can be measured by the MM scanner and made into an image.

Not intended to be limiting, in some embodiments, the nuclei that are responsible for producing the NMR signals are hydrogen nuclei (protons) in water. For example, when imaging human body, water accounts for about 60-50% of the body weight. Protons in different body tissues return to their normal spins at different rates, so the MRI scanner can distinguish among tissues. The nuclei that can be utilized for MR imaging and analysis described above are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

In some embodiments of the present disclosure, the multi-modality imaging system further comprises modules and components for performing positron emission tomography (PET) imaging and analysis. The term "positron emission tomography or PET" as used herein refers to a non-invasive radiology procedure applicable to a target body that generates image information reflecting or corresponding to functional processes taking place in the internal body.

During a PET scan or study, a PET tracer molecule is first introduced into the target body before an imaging session begins. The term "PET tracer" or "tracer" as used herein refers to a substance that may undergo certain changes under the influence of an activity or functionality within the target body, which activity and functionality are to be visualized and studied by the PET. Such changes can be chemical and/or physical, during which the PET tracer emits positrons, namely the antiparticles of electrons. A positron has the same mass and the opposite electrical charge as an electron, and it undergoes annihilations with an electron (that naturally exists in abundance within the target body) as the two particles collide. Typically, the electron-positron annihilations results in two 511 keV gamma photons, which upon their own generation, begin to travel in opposite directions with respect to one another. The PET imaging modules of the present system obtains the trajectory and dose information of the gamma photons to determine the location and concentration of the PET tracer molecules within the target body.

Many basic elements that make up organic matters have positron-emitting isotopes, including but not limited to carbon ($^{11}C$), nitrogen ($^{13}N$), oxygen ($^{15}O$) and fluorine ($^{18}F$). Accordingly, in some embodiments, the PET tracer molecules of the present disclosure are organic compounds containing one or more of those positron-emitting isotopes. These type of PET tracer molecules are either similar to naturally occurring substances or otherwise capable of interacting with the functionality or activity of interest within the target body. Hence, distributional information of the PET tracer can be reliably used as an indicator of the target body functionality.

For example, in some embodiments of the present disclosure, the PET tracer molecule is $^{18}F$-fluoro-deoxy-glucose ($^{18}F$-FDG), a radioactive analogue of glucose. $^{18}F$-FDG follows a similar metabolic pathway to glucose in vivo, but remains trapped within tissues. Thus, in vivo distribution of $^{18}F$-FDG mapped by the present PET imaging will indicate glucose metabolic activity, which can be of particular interest in oncology as proliferating cancer cell have higher than average rate of glucose metabolism. In other embodiments, the PET tracer molecule is $^{13}N$—$NH_3$ for functional imaging of myocardial perfusion. Particularly, in these embodiments, in vivo distribution of $^{13}N$—$NH_3$ can be used to distinguish between viable and non-viable tissue in poorly perfused areas of the heart, which information can be of particular interest in cardiology to identify candidates for coronary by-pass surgery.

Further provided below is a non-exhaustive list of exemplary embodiments of organic PET tracers that can be used in connection with the present system. Particularly, In some embodiments, the PET tracer molecule is $^{11}$C-methionine, where it acts as a marker for protein synthesis in oncology. In some embodiments, the PET tracer molecule is $^{11}$C-flumazenil, where it acts as a marker for benzodiazepine receptor activity in epilepsy. In some embodiments, the PET tracer molecule is $^{11}$C-raclopride, where it acts as a marker for D2 receptor agonist activity for diagnosis of movement disorders. In some embodiments, the PET tracer molecule is $^{15}$O-carbon dioxide or $^{15}$O-water, where it acts as a marker for blood perfusion in brains. In some embodiments, the PET tracer can be $^{18}$F-fluoride ion, where it acts as a marker for bone metabolism in oncology; in some embodiments, the PET tracer molecule is 18F fluoro-mizonidazole, where it acts as a marker for hypoxia in assessing patient response to radiotherapy in oncology. Yet, in other embodiments, multiple different PET tracers can be used in combination to produce complementing sets of functional data.

The above types of imaging modalities that may be included in the present system are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

FIG. 1 is an illustration of an imaging system according to some embodiments of the present disclosure. As shown in the figure, the imaging system comprises an imaging device 101, a temperature control mechanism 104, a reconstruction processor 105, a memory 106, a terminal 107, and a controller 103. The imaging device 101 may comprise one or multiple detector components 301 (see e.g. FIG. 3). The imaging device 101 is capable of examining a target body 102.

In some embodiments, the imaging device 101 is capable of acquiring imaging information of the target body 102 and converting the collected information into a format or form workable by a processor. For example, in some embodiments, the imaging information is converted into a digital form and subsequently processed. In some embodiments, the imaging device 101 is further capable of various operations, including but not limited to data preprocessing and/or data transmitting.

In some embodiments, the reconstruction processor 105 is configured to receive imaging data from the imaging device 101 and reconstruct images of the examined target body 102. According to the present disclosure, the reconstruction processor 105 may include any processor-based and/or microprocessor-based units. Merely by way of example, the processor may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or any combination thereof. The exemplary types of processors that may be used in connection with the present system are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

In some embodiments, the reconstruction processor 105 may use a reconstruction algorithm to reconstruct the imaging data received. The reconstruction algorithm may be an analytic reconstruction algorithm, an iterative reconstruction algorithm, or based on compressed sensing (CS). Analytic reconstruction algorithms may be a filter back projection (FBP) algorithm, a back projection filter (BFP) algorithm, a ρ-filtered layergram, or the like. Iterative reconstruction algorithms may be an ordered subset expectation maximization (OSEM) algorithm, a maximum likelihood expectation maximization (MLEM) algorithm, or the like. The exemplary reconstruction algorithms provided above are not exhaustive or limiting. The reconstruction algorithms that can be used in connection with the present system described herein are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

According to the present disclosure, the memory 106 is capable of storing data. The data to be stored may be from the imaging device 101, the reconstruction processor 105, and/or the terminal 107. Exemplary types of data that may be stored include raw data acquired by the imaging device 101 and reconstructed data or images generated from the reconstruction processor 105, etc. The memory 106 may comprise a plurality of components. In some embodiments, the memory 106 comprises a hard disk drive. In some embodiments, the memory 106 comprises a solid-state drive. In some embodiments, the memory 106 comprises a removable storage drive. Merely by way of examples, a non-exhaustive listing of removable storage drives that may be used in connection with the present disclosure includes a flash memory disk drive, an optical disk drive, or the like, or a combination thereof.

According to the present disclosure, the terminal 107 may be configured to receive input and/or display output. In some embodiments, the terminal 107 is configured to communicate with the imaging device 101, the reconstruction processor 105, and/or the controller 103, thus allow an end user of the system to control the production and/or display of images. The terminal 107 may include, for example, a display, a mobile device (e.g., a smart phone, a tablet, a laptop computer, or the like), a personal computer, other devices, or the like, or a combination thereof. Other devices may include a device that works independently to the imaging system, and a processing unit or processing module assembled thereupon (e.g., an intelligent home terminal). In some embodiments, the terminal 107 is configured to receive an input. For example, the terminal 107 may comprise an input device and/or a user interface (not shown in the figure), etc. Particularly, in various embodiments, the input device may be a keyboard, a touch screen, a mouse, a remote controller, or the like, or any combination thereof. An input device may include alphanumeric and other keys that may be inputted via a keyboard, a touch screen (for example, with haptics or tactile feedback), a voice-command input, an eye tracking input, a brain monitoring system, or any other comparable input mechanism. The input information received via the input device may then be communicated to the reconstruction processor 105 via, for example, a data bus, for further processing. Other types of input devices include a cursor control device, such as a mouse, a trackball, or cursor direction keys to communicate direction information and command selections to, for example, the reconstruction processor 105 and to control cursor movement on a display device. In some embodiments, the terminal 107 is configured to display output. Exemplary output information includes but is not limited to an image after image processing, a request for input or parameter relating to image acquisition and/or processing, or the like, or a combination thereof. Exemplary display devices include but are not limited to a liquid crystal display (LCD), a light emitting diode (LED)-based display, a flat panel display or curved screen (or television), a cathode ray tube (CRT), or the like, or a combination thereof.

According to the present disclosure, the controller 103 may be configured to control different components of the imaging system in order to achieve optimal analysis of the target body. In some embodiments, the controller 103 is configured to receive signals or instructions from or send information to the imaging device 101, the temperature control mechanism 104, the reconstruction processor 105, the memory 106, the terminal 107, and/or other modules or units in the system. In some embodiments, the controller 103 is capable of controlling the imaging device 101. For example, the controller 103 may control the position of the detector component 301, the position and rotational speed of the target body 102 relative to the system. In some embodiments, the controller 103 is configured to control data storage of the imaging system, including but not limited to the location of data storage, the content of data, and the method of data storage. For example, in one embodiment, the controller 103 can determinate when and/or in which format imaging data should be stored in the memory 106, and whether the imaging data or output data of the reconstruction processor 105 should be stored in the memory 106. In some embodiments, the controller 103 is configured to control the reconstruction processor 105. For example, the controller 103 can control the reconstruction processor 105 to select different reconstruction algorithms and/or correction algorithms to process the imaging data. In some embodiments, the controller 103 may send commands to the terminal 107. For example, in some embodiments, the controller 103 can transmit commands to the terminal 107, specifying the size of an image, the location of an image, or the time duration an image is to be displayed on a screen. In some embodiments of the present disclosure, the image may be divided into several sub-portions for display, and the controller 103 may control the division of sub-portions. It should be noted that the above description regarding the controller 103 are merely exemplary, and not intended to limit the scope of the present disclosure. Persons of ordinary skills in the art, after understanding the principles of the present disclosure, may envisage other variations and modifications under the teachings of the present disclosure without inventive activity, and the present disclosure is intended to cover those variation and modifications as falling under its scope.

According to the present disclosure, the present system comprises a temperature control mechanism 104 to control the operational temperature of the system. Particularly, in some embodiments, the temperature control mechanism 104 is used to control the temperature of one or more system components or at one or more system locations. For example, in some embodiments, the temperature control mechanism 104 is used to maintain the operational temperature of the imaging device 101 within a suitable range.

In some embodiments, the temperature control system achieves its function by providing a heat exchange mechanism for a target component or at a target location. For example, in various embodiments, the temperature control system comprises a fluidic heat exchange media, which preferably has a large thermal capacity. The temperature control system may further comprise corresponding devices for housing the heat exchange media, adjusting the temperature of the heat exchange media, and/or driving circulation of the heat exchange media within the system. For example, in some embodiments, the temperature control system comprises a channel that enables the heat exchange media to flow to the close vicinity of the target component or location. Then the flowing heat exchange media continuously exchanges heat with the local environment, maintaining the local temperature within a suitable range.

The imaging system may further comprise other components that are not depicted in the figure. For example, in some embodiments, the imaging system further comprises a target body support (not shown) for holding the target body in place and/or moving it to a proper position during examination. In some embodiments, the target body support may be under automatic control of the controller 103. Alternatively or additionally, the target body support may be manually controlled by an end user of the imaging system. In some embodiments, the target body support can be a patient table (see e.g. FIG. 5) where a human patient may lie on his/her back or in a prone position.

It should be noted that the imaging system described above is provided for the purpose of illustration, and not intended to limit the scope of the present disclosure. Apparently for persons having ordinary skills in the art, numerous variations and modifications may be conducted under the teaching of the present disclosure without inventive activity. And the present disclosure is intended to encompass all those variations and modifications as falling under its scope.

Figure 2:
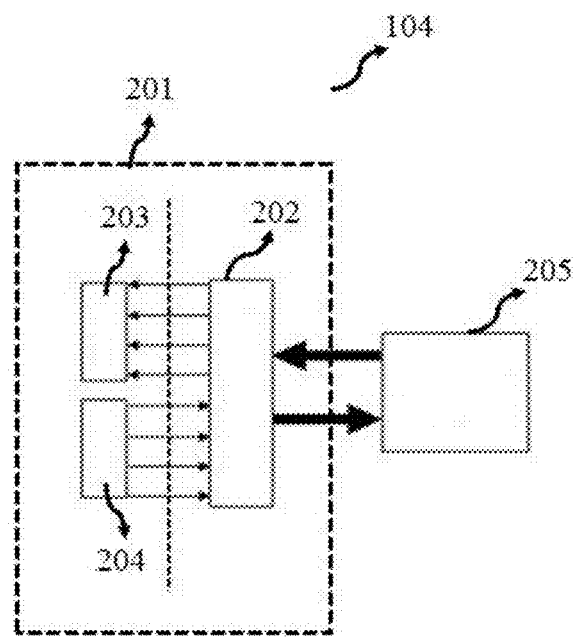
FIG. 2 illustrates a cooling system according to some embodiments of the present disclosure.

FIG. 2 illustrates an exemplary temperature control mechanism according to some embodiments of the present disclosure. The temperature control mechanism 104 comprises a circulation system 201 and a cooling apparatus 205. The circulation system 201 further comprises an inlet 203, an outlet 204 and a distribution system 202. The distribution system 202 is capable of distributing heat exchange media provided by the cooling apparatus 205 into different inlets 203 and collecting heat-absorbed heat exchange media flowing out of the outlet 204 into the cooling apparatus 205. The cooling apparatus 205 is coupled to the circulation system 201 and configured to provide heat exchange media to the circulation system 201. The cooling apparatus 205 may also comprise mechanisms to recycle the heat-absorbed coolant and dissipate the heat. It should be noted that the temperature control mechanism described above is provided for the purpose of illustration, and not intended to limit the scope of the present disclosure. Apparently for persons having ordinary skills in the art, numerous variations and modifications may be conducted under the teaching of the present disclosure without inventive activity. And the present disclosure is intended to encompass all those variations and modifications as falling under its scope.

In some embodiments, a PET imaging modality of the present system contains a specifically designed PET detector that detects the gamma ray signals emitted from the target body. Particularly, during a PET scan or study, a PET tracer molecule is first introduced into the target body before an imaging session begins. After the administered tracer reaches a suitable distribution and/or concentration within the target body, data acquisition may begin. Particularly, the target body is placed within a sample area surrounded by a number of PET detector modules of a PET detector. The detector modules are capable of registering incident gamma rays. As the radionuclide in the PET tracer molecule decays, the resulting positrons subsequently annihilate on contact with electrons in the nearby environment in the target body. Each annihilation produces two 511 keV photons that travel in opposite directions and become detected by the surrounding detector modules. Two detection events that unambiguously occur within a certain time window are recognized by the PET detector to be coincident, and thus are determined to have come from the same annihilation. These coincidence events can be stored in arrays corresponding to projections through the target body and reconstructed using tomographic technologies. The resulting images show the tracer distribution throughout the target body.

The term "PET detector" or "PET detector module" as used herein refers to an electrical component or combination of multiple electrical components capable of receiving the gamma-ray signal and converting it into a form of signal that can be processed and analyzed by a processor, such as a computer. Particularly in some embodiments, the original gamma ray signal may undergo several rounds of conversions before it is eventually turned into a form workable by a computer. The sequential conversions can be achieved by synergic operations of multiple electrical components of a PET detector block, or by a single multi-functional component.

For example, in some embodiments, the gamma ray radiation is first converted into the form of visible or invisible light, and then into an analog or digital signal that is to be processed by a computer. Particularly, in some of these embodiments, the PET detector contains a component capable of absorbing gamma-ray radiation and emitting a fraction of the absorbed energy as lower-energy photons of ultraviolet or visible wavelength, and another component is capable of sensing the light signal and converting it into an electrical signal. More particularly, in some of these embodiments, the component responsible for the conversion is a scintillator, such as a scintillation crystal block.

The terms "scintillator" as used herein broadly relates to any material that has the ability to absorb ionizing radiation and to emit a fraction of the absorbed energy as light. For example, a gamma photon incident on the scintillator creates an energetic electron, either by Compton scatter or by photoelectric absorption; as the electron passes through the scintillator, it loses energy and excites other electrons in the process; these excited electrons decay back to their ground state, giving off light as they do so. As such, the scintillator produces a brief pulse of visible or ultraviolet photons corresponding to each gamma photon that interacts with the scintillator material. The intensity of the light pulses is proportional to the gamma energy deposited in the scintillator.

The scintillator to be used in connection with the present system can be made of various types of materials working under different principles, which include but are not limited to organic or inorganic, crystalline or non-crystalline, liquid, gas or solid materials. Preferably, a suitable scintillator material to be used in connection with the present system is of a high density and radiation hardness, capable of a fast operation speed, and has a low production cost. More preferably, a suitable scintillator material provides a short decay time and high light output, thereby capable of reducing a required PET scan time. Further preferably, a suitable scintillator material has a high detection efficiency for gamma-ray radiation, such that the target body, particularly a patient or live animal subject, can be exposed to a shortened scan time and a lowered PET tracer dose, thereby reducing the risk and undesirable side effects to the patient. Further provided below is a non-exhaustive list of exemplary embodiments of suitable scintillator materials: $CdWO_4$, $BaF_2$, CsF, CsI(Na), CsI(Tl), NaI(Tl), $CaF_2(Eu)$, lutetium oxyorthosilicate (LSO) crystals; bismuth germinate (BGO) crystals, gadolinium oxyorthosilicate (GSO) crystals, LYSO crystals, and mixed lutetium silicates (MLS) crystals.

In some embodiments, the PET detector contains a separate set of electrical components, collectively referred to as a photodetector, which senses the light pulses emitted from the scintillator and converts them into a corresponding electrical signal that can be further analyzed by a processor. In some embodiments, components of a photodetector are configured to comprise a photoelectric converter. A photoelectric converter is capable of absorbing energy of light and re-emit the absorbed energy in the form of electrons. Exemplary embodiments of a photoelectric converter that can be used in connection with the present system include Photomultiplier Tube (PMT), Avalanche Photodiode (APD), Single-Photon Avalanche Photodiode (SPAD), Silicon Photomultiplier (SiPM), Digital Silicon Photomultiplier (DSiPM). The photodetector that can be used in connection with the present system described above are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

In some embodiments, components of a photodetector are configured to comprise a set of frontend electronics and a set of readout electronics. The frontend electronics may comprise various amplifiers, filters, and analog-to-digital converters. While in use, the frontend electronics collect the electrical signals generated by a photoelectric converter, perform signal conditioning, and output digital signals. In some embodiments, positional coupling between the frontend electronics and the scintillator is preferred to be precise, stable and tight.

The readout electronics, on the other hand, may further process and/or analyze the information collected and communicated by the frontend electronics. In some embodiments, the readout electronics collect at least the position sensitive information regarding each gamma photon incident on the scintillator. For example, in some embodiments, the readout electronics are at least capable of identifying the scintillator block that captured the gamma ray, performing positional decoding within the scintillator block to determine the trajectory and incident depth of the gamma photon, measuring the energy deposition in the scintillator block and/or recording the time of incident. In various embodiments, the readout electronics may be configured to amplify and/or purify the signals, to analyze if a detection event is to be accepted, and/or to determine if two detection events are coincident. For example, in some embodiments, the readout electronics are configured to match gamma ray detections as potential coincidence events. When two gamma rays strike detectors approximately opposite one another, it is possible, absent the interactions of random noise and signal gamma ray detections, that a positron annihilation took place somewhere along the line between the detectors.

While in operation, local temperature of a PET detector module may increase significantly (such as reaching 40-50 degree centigrade), bringing down functionalities of some temperature-sensitive components. Accordingly, in some embodiments, a PET detector module further comprises a temperature control mechanism. For example, in some embodiments, temperature control is achieved by providing a heat exchange mechanism within the local environment, which is configured to remove heat from particular components or locations.

In some embodiments, the PET detector module further comprises a positioning mechanism for holding various components at desirable locations. For example, in some embodiments, the positioning mechanism is capable of pressing the frontend electronics and the scintillator together for precise, stable and tight positional coupling between the two. In some embodiments, the positioning mechanism is configured to hold the heat exchange mechanism in a suitable position relative to a specific component(s) or location(s) within the PET detector module, thus to achieve optimal efficiency of heat exchange. In some embodiments, the positioning mechanism facilitates heat exchange between PET components and the heat exchange mechanism.

Figure 3:
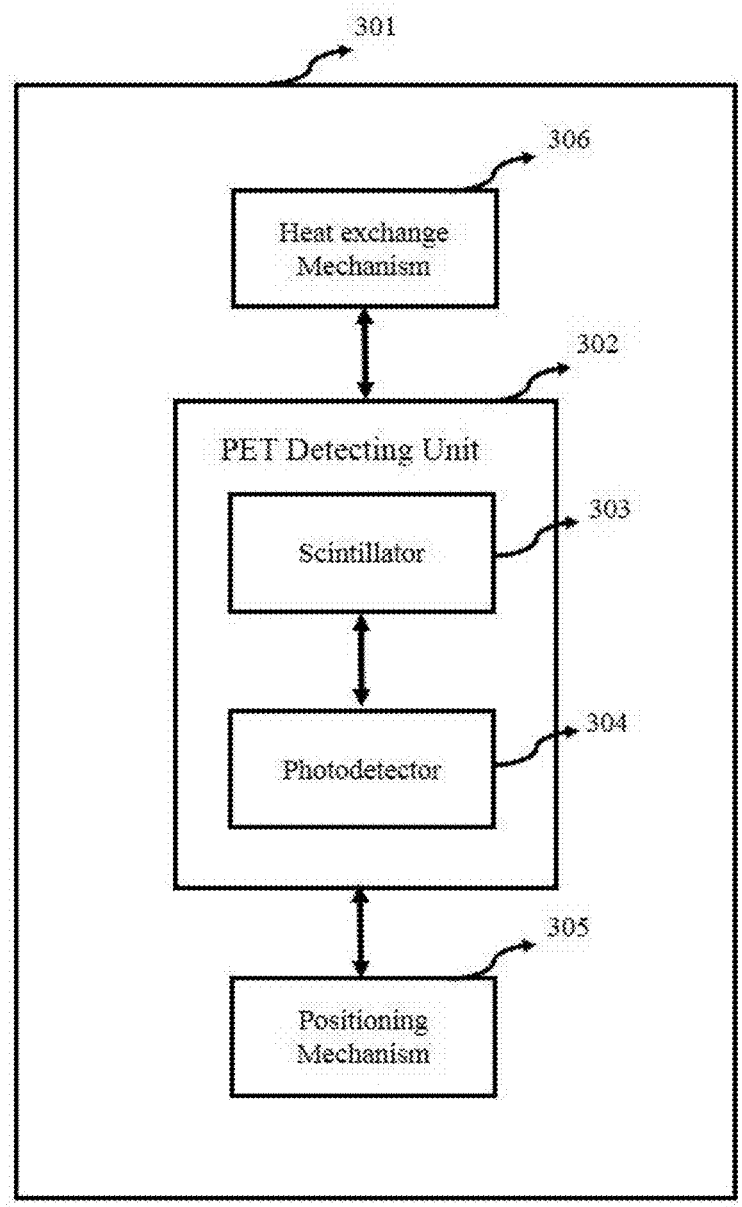
FIG. 3 is a schematic illustration of a PET detector module according to some embodiments of the present disclosure.

FIG. 3 is an illustration of a PET detector module according to some embodiments of the present disclosure. As shown in the figure, the PET detector module 301 comprises a heat exchange mechanism 306 and various electronic and/or non-electronic components collectively referred to as a PET detecting unit 302. Particularly, as shown in FIG. 3, the detecting unit 302 comprises a scintillator 303 and a photodetector 304. In some embodiments, the photodetector comprises a set of frontend electronics and a set of readout electronics (not shown in FIG. 3). The PET detector module 301 further comprises a positioning mechanism 305 for holding various components in place. In this embodiment, the heat exchange mechanism 306 is configured to monitor and/or control the temperature of the various components in the detecting unit 302 simultaneously. The position mechanism may be configured to facilitate heat exchange within the PET detector module.

According to the present disclosure, the heat exchange mechanism 306 is capable of transferring heat between objects. The heat transferring objects may be spatially separated or in direct contact. In various embodiments, the heat exchange mechanism 306 enables a fluidic heat exchange media to flow to the close vicinity of the heating-producing component or location in a PET detector module. Then the flowing heat exchange media continuously exchanges heat with the local environment, maintaining the local temperature within a suitable range. In various embodiments of the present disclosure, the heat exchange mechanism may be a shell and tube heat exchanger, a plate heat exchanger, a plate fin heat exchanger, a pillow plate heat exchanger, a fluid heat exchanger, or any other types of heat exchanger that are familiar to people having ordinary skills in the art. The heat exchanger may be made of suitable metal, nonmetal and/or alloy materials that are currently available in the field or to be discovered or made in future.

Figure 4A:
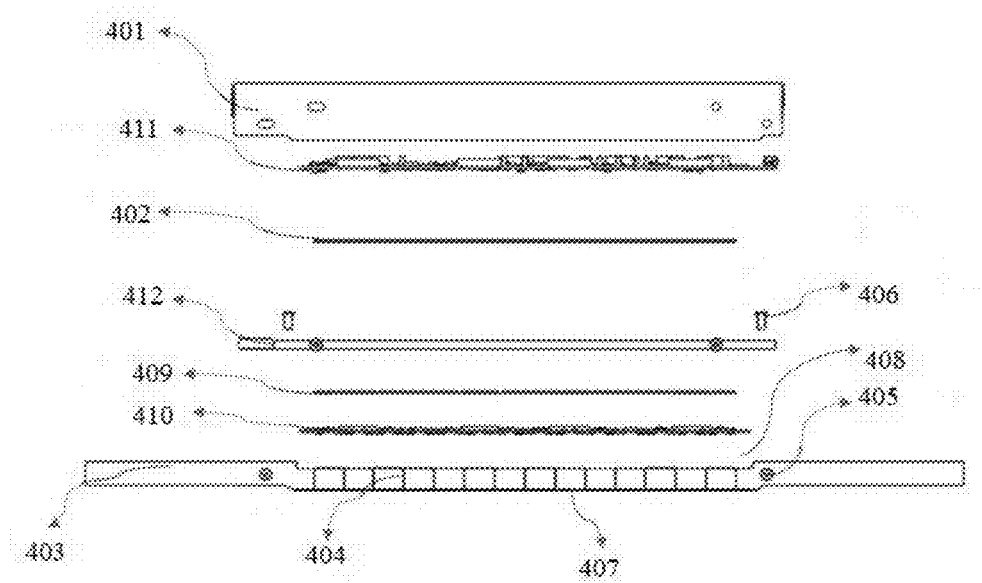
FIGS. 4A and 4B illustrate a specific embodiment of a PET detector module according to the present disclosure. Particularly, in this embodiment, the PET detector module comprises a heat exchange plate for temperature control.

FIG. 4A illustrates a specific embodiment of a PET detector module according to the present disclosure. As shown in the figures, the PET detector module comprises a shield 401, a set of readout electronics 411, a first thermal conductive layer 402, a heat exchange plate 412, a second thermal conductive layer 409, a set of front-end electronics 410, a scintillator 404, a pair of fixation blocks 403, and a supportive layer 407. The PET detector module further comprises other fixation parts for holding various PET components in place. For example, the particular embodiment as shown in FIG. 4A comprises a pair of heat exchange plate fixing screws 406 and shield fixing screws 405.

According to the present disclosure, the heat exchange plate 412 functions as the heat exchange mechanism for controlling the temperature of the PET detector module during operation. For example, in some embodiments, the heat exchange plate 412 is used to dissipate heat generated by the electronics within the PET detector module, thus bringing down the temperature. Alternatively, in other embodiments, the heat exchange plate 412 may be used to bring external heat into PET detector module, thus increasing the working temperature. Accordingly, in some embodiments, fabrication material(s) of the heat exchange plate is low heat resistant and preferably has a good thermal conductivity.

In a PET/MR hybrid system, placement of PET components within the MR magnetic fields may interfere with the performance of the MR imaging modality. For example, MR magnetic gradients may induce eddy currents in conductive materials of the PET components, which could in turn distort the MR gradient field. Accordingly, in some embodiments, fabrication material(s) of the heat exchange plate 412 has a low magnetic susceptibility.

According to the present disclosure, the heat exchange plate 412 can be made of a metallic material, a nonmetallic material, an alloy material, or a combination thereof. In some embodiments, the heat exchange plate 412 can be made of a non-ferromagnetic material such as copper, aluminum, aluminum alloy, alloy steel, and carbon fiber. In some embodiments, the heat exchange plate 412 can be made of a thermal conductive polymer such as epoxy, plastic, silicon, resin and rubber. In some embodiments, the heat exchange plate 412 can be made of an organic material. In various embodiments, the heat exchange plate 412 can be made of one material or multiple materials. For example, the heat exchange plate 412 can be made of ceramics. Fabrication materials described above are not exhaustive and are not limiting. Additional materials suitable for the purpose of the present disclosure, either readily available or to be discovered or made in future, may be ascertained to one skilled in the art, and it is intended that the present disclosure encompass all such materials as falling within the scope of the present disclosure.

Dimensions of the heat exchange plate 412 are selected such that it fits well with the typically limited space in a PET detector module. In some embodiments, the heat exchange plate 412 is about 2 to 20 millimeters thick. In some embodiments, the heat exchange plate 412 is about 5 to 6 millimeters thick.

Metallic or alloying materials with good heat exchange efficiency may be used to fabricate the heat exchange plate. However, placing a metal heat exchange plate into close vicinity of PET electronics within the typically limited space of a PET detector module may cause undesirable consequences, such as creating short circuits between the electronics. Thus, as shown in FIG. 4A, the PET detector module further comprises thermal conductive layers (402, 409) that are placed between the heat exchange plate 412 and the PET electronics (410, 411). Particularly, the first thermal conductive layer 402 is positioned between the readout electronics 411 and the heat exchange plate 412. The second thermal conductive layer 409 is positioned between the front-end electronics 410 and the heat exchange plate 412.

Particularly, in some embodiments, the thermal conductive layers (402, 409) are made of an insulating material(s) with a good thermal conductivity. For example, in some embodiments, the thermal conductive layers (402, 409) have a heat conduction coefficient greater than that of the air, and are used to seal the air gap between the heat exchange plate 412 and PET electronics (410, 411) positioned on each side of the heat exchange plate 412. Thus, in these embodiments, the thermal conductive layers (402, 409) increase the efficiency of heat exchange between the heat exchange plate 412 and PET electronics (410, 411) by bringing them into close contact with each other. Particularly, in some embodiments, the thermal conductive layers (402, 409) are made of thin-film material. In some embodiments, the thermal conductive layers (402, 409) are made of silicon, resin, a cooling gel or other suitable materials currently available in the field or to be made in future. In some embodiments, the first thermal conductive layer (402) and the second thermal conductive layer (409) are made of a same material. Alternatively, in other embodiments, the first thermal conductive layer (402) and the second thermal conductive layer (409) are made of different materials.

In some embodiments, the thermal conductive layers (402, 409) connect the heat exchange plate 412 with all the electronics (410, 411) within a PET detector module. Alternatively, in other embodiments, the thermal conductive layers (402, 409) connect the heat exchange plate 412 to selected parts of the frontend electronics (410) and/or the readout electronics (411). In some embodiments, the thermal conductive layers (402, 409) further connect the heat exchange plate 412 to non-electronic components or locations of the PET detector module. Particularly, the selection of target component and/or location may be based on various considerations, such as temperature sensitivity of the target component or heat production rate at the target location, etc. Further, in these embodiments, the thermal conductive layers (402, 409) further play a role in positioning various components of the PET detector module.

Figure 4B:
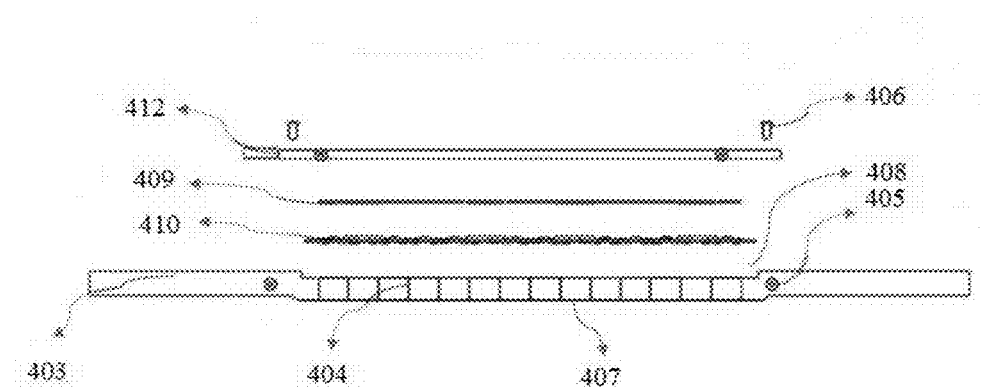

As disclosed above, the frontend electronics 410 are configured to collect position sensitive information of gamma ray incident on the scintillator. In some embodiments, the thermal conductive layers (402, 409) further function to position the frontend electronics 410 and the scintillator 404 in precise positions relative to each other. Particularly, in some embodiments, one or both of the thermal conductive layers (402, 409) is made of a compressive material(s) having a compressive surface. The compressive layer extends the compressive surface towards the frontend electronics such that the compressive surface presses the frontend electronics against the scintillator. For example, as shown in FIG. 4B, the layered structures of the PET detector module (including the heat exchange plate 412, the second thermal conductive layer 409, the frontend electronics 410 and the scintillator 404) are to be assembled in a compact fashion. That is, the assembly thickness of these components is smaller than the sum of respective thicknesses of the individual components. Hence, after assembly, the second thermal conductive layer 409 exerts a compressive force that presses the frontend electronics 410 firmly against the scintillator 404, stabilizing the contact and communication between the two. In some embodiments, the thermal conductive layer 409 is made of a compressive material, such as silicone rubber, or any suitable materials currently available in the field or to be discovered or made in future. The suitable materials may be thermal conductive, electrical insulating, and of good compression property. In some embodiments, the thermal conductive layer may be made of metallic materials. A non-exclusive list of metallic materials that may be used to make the thermal conductive layer includes aurum, argentum, copper, aluminum, magnesium, and stannum. In some embodiments, the thermal conductive layer may be made of polymer materials. A non-exclusive list of polymer materials that may be used to make the thermal conductive layer includes polyethylene (PE), polyvinyl chloride (PVC), poly propylene (PP), acrylonitrile butadiene styrene (ABS), polyamide, rubber, and epoxy. In some embodiments, the thermal conductive layer may be made of inorganic non-metallic materials. A non-exclusive list of inorganic non-metallic materials that may be used to make the thermal conductive layer includes carbon, silicon, silicon dioxide, silicon carbide, aluminum nitride, gallium arsenide, aluminum oxide, diamond and graphite. Besides, composite materials containing one or multiple of metallic materials, polymer materials, inorganic non-metallic materials, and/or any combination thereof, may also be suitable for making the thermal conductive layers. Exemplary composite materials that may be used to make the thermal conductive layers include carbon nanotube aluminum matrix composites comprising aluminum and carbon, thermal adhesives comprising epoxy and stannum, thermal conductive resin comprising epoxy and silicon dioxide, thermal conductive silicone rubber comprising rubber, silicon, and/or resin. Thermal conductive plastics comprising polymers and inorganic non-metallic materials may also be suitable for making the thermal conductive layer. Thermal conductive plastics may comprise polymers such as PE, PVC, PP, ABS and PA. Thermal conductive plastics may comprise inorganic non-metallic materials such as silicon dioxide, silicon carbide, aluminum nitride, gallium arsenide, and aluminum oxide. It should be noted that the materials that may be suitable for making the thermal conductive layer described above is provided for illustrative purposes only, and is not intended to limit the scope of the present disclosure. Apparently for persons having ordinary skills in the art, numerous variations and modifications may be conducted under the teaching of the present disclosure. However, those variations and modifications are still within the scope of the present disclosure.

Particularly, as shown in FIG. 4B, the PET detector module comprises a pair of fixation blocks 403. The scintillator 404 comprises an array of scintillator crystals glued in a row between the two fixation blocks 403. A supportive layer 407 connects with the fixation blocks 403 and supports the scintillator crystal array 404. Each fixation block 403 has a step-like shape at the end proximate to the scintillator crystal array 404. The scintillator crystal array 404 is assembled between the lower steps. The heat exchange plate 412 is assembled on the higher steps by, for example, a pair of screws 406, thus leaving a thin cavity 408 between the heat exchange plate 412 and the scintillator crystal array 404. The cavity 408 has the thickness of the fixation block step. The cavity 408 houses the frontend electronics 410 and the thermal conductive layer 409. The thickness of the cavity 408 is smaller than the sum of the thicknesses of the frontend electronics 410 and the thermal conductive layer 409 in its non-compressed form.

After assembly, the thermal conductive layer 409 presses the frontend electronics 410 against one surface of the scintillator crystal array 404, while the supportive layer 407 supports the scintillator crystal array 404 from the opposing surface. In some embodiments, the supportive layer 407 is made of a material(s) capable of affording sufficient physical support at a small thickness, and does not block gamma ray at any substantial level. The supportive layer 407 can be made of any suitable materials currently available in the field or to be discovered or made in future. For example, in some embodiments, the supportive layer 407 is made of carbon fiber. In some embodiments, the supportive layer 407 is made of metals of low density. For example, the supportive layer 407 may be made of thin aluminum plate. In alternative embodiments, the supportive layer 407 is optional if the strength of scintillator crystals satisfies actual needs.

According to the present disclosure, the compressive surface of a thermal conductive layer may be continuous or discontinuous, and the compressive force may be uniform or non-uniform across the compressive surface. For example a thermal conductive layer (402, 409) may be made of a compressive material(s) entirely or only in some portions. The selected portions where a compressive material(s) is used are where compressive forces are needed after assembly. Accordingly, compressive forces provided at different portions of a thermal conductive layer (402, 409) may be uniform or non-uniform. A thermal conductive layer (402, 409) may be designed to provide different compressive forces at different locations according to specific designs of the frontend electronics (410). For example, a stronger compressive material may be used at a location where a stronger force is preferred. Alternatively, a thicker block of compressive material may be used at a location where a stronger force is preferred.

In some embodiments, a shield 401 may be used for protecting the PET detector module from environmental impact. The shield 401 may be assembled on the fixation blocks 403, for example, by a pair of screws 405.

Figure 5:
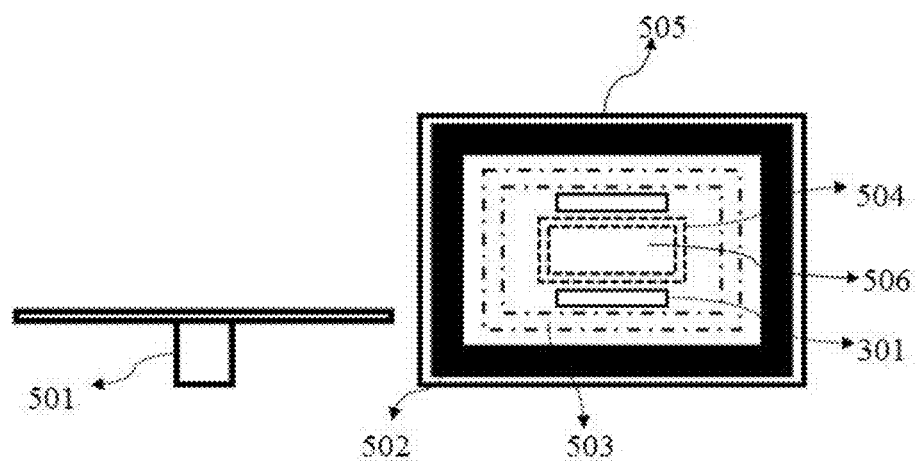
FIG. 5 illustrates a PET/MR hybrid system according to some embodiments of the present disclosure.

In some embodiments, the PET detector module is to be used in a multi-modality imaging system comprising both PET and MR functionalities. FIG. 5 illustrates an exemplary structure of a PET/MR hybrid system. Particularly, as shown in the figure, the system comprises an imaging gantry 505 and a patient table 501 for supporting and moving a target body within the imaging gantry 505. The MR imaging modality comprises a main magnet 502, a gradient coil 503, a radio frequency coil 504, all arranged within the imaging gantry 505. The PET imaging modality comprises a PET detector, which includes at least a pair of PET detector modules 301 also placed within the imaging gantry 505. The pair of PET detector modules 301 have their respective scintillator faces opposing each other, and flank a sample space 506 within the imaging gantry 505 where the target body is to be placed.

The PET detector used in connection with the PET imaging modality may comprise various configurations. In some embodiments, the PET detector may comprise four PET detector modules forming a cubic column configuration. The four detector modules surround the sample area in a cubic column configuration with each detector module perpendicular to two other detector modules. In some embodiments, the PET imaging modality may comprise multiple PET detector modules forming a barrel configuration, wherein the center of the barrel may coincide with the center of the imaging gantry 505. In some embodiments, the PET detector modules may be integrated into the MR imaging modality. For example, the PET detector modules may be integrated between the radio frequency coil and the gradient coil of the MR imaging modality. In alternative embodiments, the PET detector is configured as a PET insert module, which may be reversibly coupled to the MR imaging system when PET functionality is needed. For another example, PET detector modules may be installed onto the patient table to image a particular portion of the target body, such as a patient's breast tissues, heads, and shoulders. The PET detector modules that can be used in connection with the present system described herein are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

In a PET/MR hybrid system, MR magnetic fields may induce eddy currents in conductive materials of the PET components, which would in turn distort the applied MR magnetic fields. Thus, functionality of both imaging modalities may be disrupted. Particularly, eddy currents are loops of electrical current induced within conductors by a changing magnetic field in the conductor. Eddy currents flow in closed loops within the conductor in planes perpendicular to the magnetic field that induced the eddy currents. By Lenz's law, an eddy current creates a magnetic field that opposes the magnetic field that created it. Thus, eddy currents react back on the source of the magnetic field. For example, magnetic fields created by eddy currents may impact on homogeneity of the main magnetic field of the MR imaging modality, which is used to polarize spins and creating magnetization. Additionally, magnetic fields created by eddy currents may distort the MRI gradient fields created by gradient coils of the MR imaging modality, producing a wide range of image artifacts, including shearing, shading, scaling, blurring, and spatial misregistration, and affecting quality of images produced by the MR imaging modality. Additionally, eddy currents flowing through conductive materials may also dissipate energy as heat in the conductor. The heat dissipated by the eddy current may further increase working temperature of the PET detector and affect the imaging quality of the PET imaging modality.

Accordingly, in some embodiments, electrical conductive PET components are designed to reduce eddy effect. For example, in some embodiments, the PET detector comprises one or more heat exchange plates 412 made of an electrical conductive material(s), such as copper and aluminum. In these embodiments, the heat exchange plate 412 is designed to reduce eddy currents by reducing the size of electrical conductive planes perpendicular to the eddy effect inducing magnetic field. Particularly, in some embodiments, one or more slots are opened on the heat exchange plate 412 to divide the conductive planes into smaller segments. A slot can be straight, cutting adjacent planes at same positions, or can be curved, cutting adjacent planes at different positions. A slot may be a partial slot having an open end and a closed end, thus dividing the heat exchange plate 412 into connected segments. A slot may be a complete slot having two open ends, thus dividing the heat exchange plate 412 into separated segments.

Figure 6:
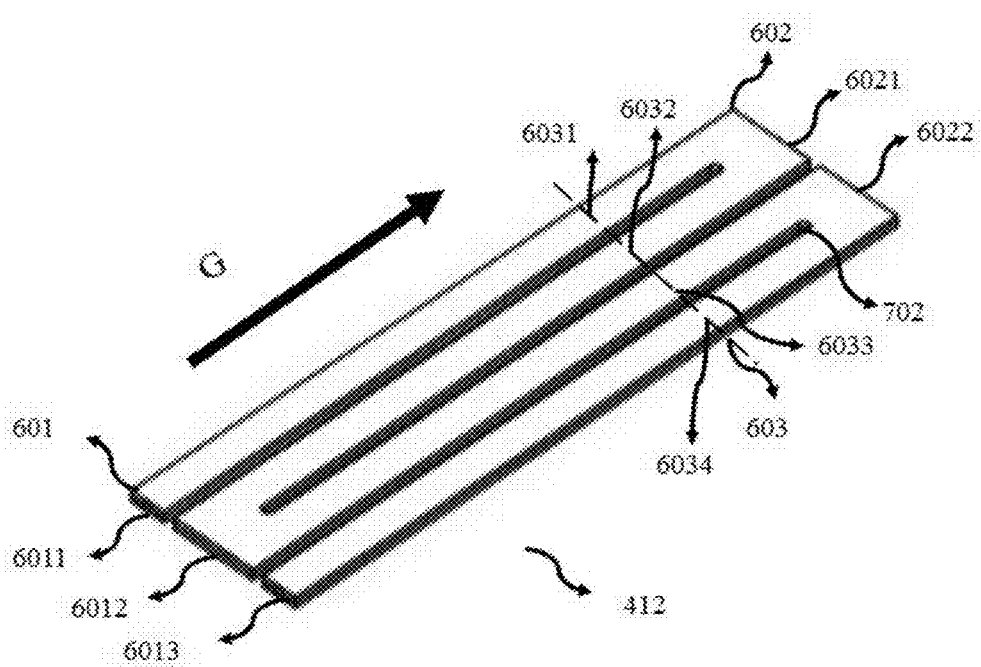
FIG. 6 illustrates the direction of a magnetic field (Bo) and relative positioning of a heat exchange plate in the magnetic field according to some embodiments of the present disclosure.

FIG. 6 illustrates the direction of a magnetic field (G) and relative positioning of a heat exchange plate having slots in the magnetic field according to some embodiments of the present disclosure. The magnetic field (G) is an eddy effect inducing magnetic field. For example, in some embodiments, the magnetic field (G) is the gradient field of the MR imaging modality. The arrow indicates the direction of G. In some embodiments, the gradient field is parallel to the main field. To reduce G induced eddy currents in the heat exchange plate 412, the heat exchange plate 412 may be slotted along the direction of G, such that conductive planes perpendicular to G are divided into smaller segments. Particularly, in the specific embodiment of FIG. 6, the heat exchange plate 412 has three straight slots 702 (see e.g. FIG.

7) each having an open end and a closed end. Adjacent slots have their respective open ends at opposing ends of the heat exchange plate 412. Thus, two open ends and one closed end are positioned at one end of the heat exchange plate 412, while one open end and two closed ends are positioned at the opposing end of the heat exchange plate 412.

As shown in FIG. 6, all three slots are parallel to G, and divide each conductive plane perpendicular to G into 2 to 4 smaller segments. As used herein, planes perpendicular to G may include not only surface planes such as surfaces 601 and 602 of the heat exchange plate 412, but also any internal conductive plane perpendicular to G. Thus, two slots divide the surface plane 601 into three segments, 6011, 6012, 6013; one slot divides the surface plane 602 into two segments 6021, 6022; and for an exemplary internal plane 603 at the location indicated by the dashed line, three slots divide it into four segments, 6031, 6032, 6033 and 6034.

The structure described above regarding the heat exchange plate is not exhaustive and are not limiting; after consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope. For example, in various embodiments, the heat exchange plate may comprise any suitable number of slots. The slots may each have one open end and one closed end or each has two open ends. Different slots may have their respective open ends at the same end of the heat exchange plate or alternatively have their respective open ends at the opposing ends of the heat exchange plate. Adjacent slots may have their respective open ends at the same end of the heat exchange plate, or alternatively have their respective open ends at opposing ends of the heat exchange plate. The slots may be filled with one or more insulating materials.

FIGS. 7A through 7D illustrate several specific embodiments of a heat exchange plate 412 according to the present disclosure. Particularly, in these embodiments, the heat exchange plate 412 comprises a tubing 701 embedded within a plate 703. The plate 703 has one or more slots 702, each slot 702 has at least an open end.

Figures 7A, 7B:
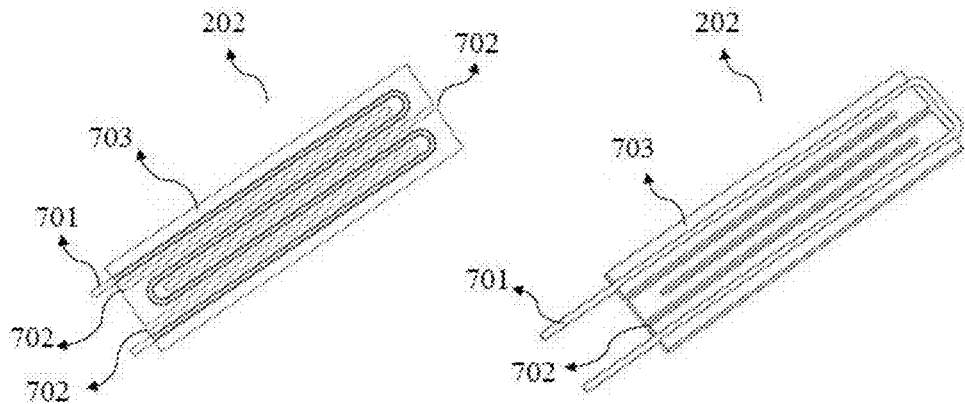
FIGS. 7A through 7D illustrate several specific embodiments of a heat exchange plate according to the present disclosure. Particularly, as shown in FIGS. 7A through 7D, in these embodiments, the heat exchange plate comprises a tubing embedded within a slotted plate.

Particularly, as shown in FIGS. 7A and 7B, the plate 703 has three slots 702, each having an open end and a closed end. Adjacent slots have their respective open ends at opposing ends of the plate 703. Thus, two open ends and one closed end are positioned at one end of the plate 703, while one open end and two closed ends are positioned at the opposing end of the plate 703. The three slots 702 divide the plate 703 into four segments, which are connected near the closed ends. In FIG. 7A, the tubing 701 runs in parallel with the slots 702 in each of the four segments, turning 180 degrees around each closed end. In FIG. 7B, the tubing 701 is partially embedded within the plate 703. Particularly, the tubing 701 runs in parallel with the slots 702 in the outer two segments, turning 180 degrees at its unembedded portion surrounding two close ends and one open end of the slots 702.

Figures 7C, 7D:
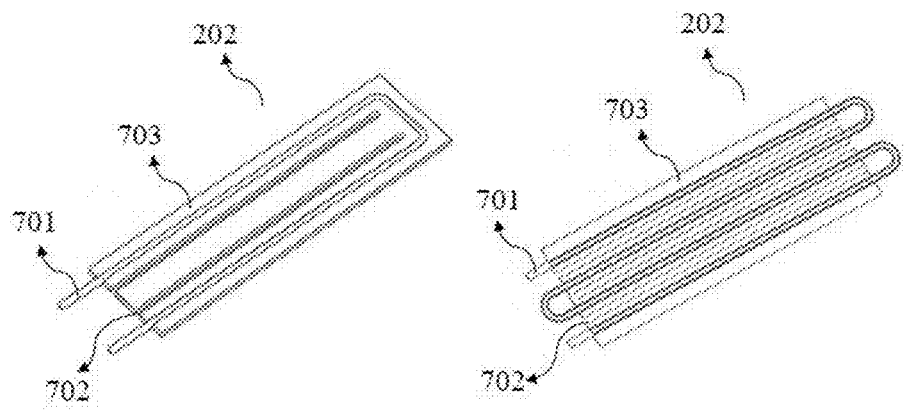

As shown in FIG. 7C, the plate 703 has two slots 702, each having an open end and a closed end. Both open ends are positioned at one end of the plate 703, while both closed ends are positioned at the opposing end of the plate 703. The two slots 702 divide the plate 703 into three segments, which are connected near the closed ends of the slots 702. The tubing 701 runs in parallel with the slots 702 in the outer two segments, turning 180 degrees surrounding both closed ends of the slots 702.

As shown in FIG. 7D, the plate 703 has three slots 702, each having two open ends. Thus the three slots 702 divide the plate 703 into four unconnected segments. Each segment has a portion of the tubing 701 embedded therein, which runs in parallel with the slots 702. At the unembedded portion, the tubing 701 turns 180 degrees around one open end of each slot 702. Particularly, open ends of adjacent slots that are surrounded by a turn of the tubing 701 are located at opposing ends of the plate 703.

The plate 703 may assume various configurations other than those described above. In some embodiments, the plate 703 may have a first surface and a second surface opposite to the first surface. The plate 703 may further comprise a front end and a rear end opposite to the front end. The first surface and the second surface may respectively extend from the front end to the rear end of the plate. The plate 703 may further comprise a slot extending along a direction from the front end to the rear end. The slot may penetrate the first surface and the second surface. In various embodiments, the slot may be blocked by the front end or the rear end. The plate 703 may comprise fluidic passage attached to the plate.

In various embodiments, the plate 703 may further define a groove. The groove may have at least one section extending from the front end to the rear end of the plate. The fluidic passage is a tubing with a corresponding part positioned in the groove. In some embodiments, the corresponding part of the tubing may be disposed between the first surface and the second surface of the plate.

FIG. 8A through FIG. 8D illustrate another exemplary embodiment of the heat exchange plate 412 according to the present disclosure. Particularly, in this embodiment, the plate 703, instead of having embedded tubing, comprises an internal channel 802.

Figure 8A:
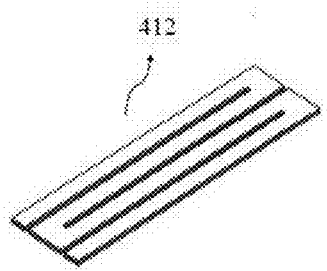
FIGS. 8A through 8D illustrate another embodiment of a heat exchange plate according to the present disclosure. Particularly, the heat exchange plate is a slotted plate having an internal channel.

FIG. 8A illustrates a perspective view of the exemplary embodiment of the heat exchange plate according to the present disclosure. As can be seen in the figure, the heat exchange plate 412 is a rectangular thin plate 703 having three slots 702. Each slot 702 has an open end and a closed end. Adjacent slots have their respective open ends at opposing end of the plate 703. Thus, two open ends and one closed end are positioned at one end of the plate 703, and one open end and two closed ends are positioned at the opposing end of the plate 703. The three slots 702 divide the heat exchange plate 703 into four segments, which are connected near the closed ends of the slots 702. The channel is internal to the plate 703, and thus is not shown in the figure.

Figure 8B:
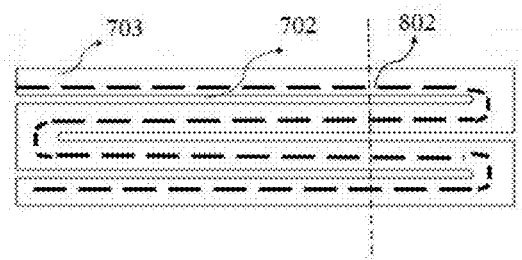

FIG. 8B illustrates a top view of the heat exchange plate according to some embodiments of the present disclosure. Particularly, the dashed line illustrates the location of the internal channel 802. As can be seen from the figure, the channel 802 runs in parallel with the slots 702 in each of the four segments, turning 180 degrees around each close end.

Figure 8C:
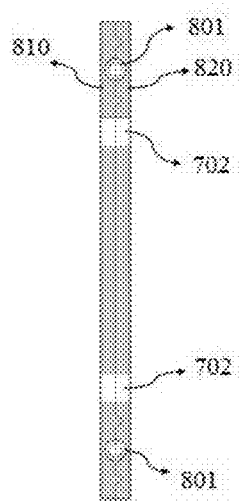

FIG. 8C is a side view of the heat exchange plate according to some embodiments of the present disclosure. Particularly, FIG. 8C shows one end of the heat exchange plate where a pair of inlet and outlet 801 of the channel 802 can be seen. Also can be seen from this view are open ends of two slots 702. As shown in the figure, in this particular embodiment, the heat exchange plate comprises two half plates (810, 820), which engage with each other to form the heat exchange plate. Each half plate (810, 820) is engraved with a groove, and when the two half plates (810, 820) engage to form the heat exchange plate 412, the two grooves seal against each other to form the internal channel 802.

Figure 8D:
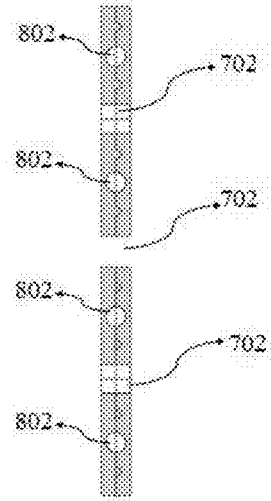

FIG. 8D illustrates a cross section of the heat exchange plate according to some embodiments of the present disclosure. Particularly, this view shows the cross section created by slicing the heat exchange plate 412 along the vertical line as shown in FIG. 8B. What can be seen from this view includes cross sections of the three slots 702, and particularly, the open end of the middle slot and the closed ends of the upper and lower slots. Also can be seen from this view is cross sections of the internal channel 802, which runs in each of the four segments divided by the slots 702.

In alternative embodiments, the heat exchange plate 412 may be manufactured as a single piece having the internal channel 802, such as by additive manufacturing like 3D printing. It should be noted that the manufacturing method described above is provided for illustrative purposes only, and is not intended to limit the scope of the present disclosure. Apparently for persons having ordinary skills in the art, numerous variations and modifications may be conducted under the teaching of the present disclosure. However, those variations and modifications are still within the scope of the present disclosure.

According to various embodiments, the plate may comprise any suitable number of slots. The slots may each have one open end and one closed end or each have two open ends. Different slots may have their respective open ends at the same end of the heat exchange plate. Alternatively, different slots may have their respective open ends at the opposing sides of the plate. Adjacent slots may have their respective open ends at the same end of the plate. Alternatively, adjacent slots may have their respective open ends at opposing ends of the plate. The slots may divide the plate into any number of connected or unconnected portions, and one or more tubing or channel may run in any number of these portions. The tubing and channel may comprise straight and/or curved portions. The tubing and channel may or may not run in parallel with the slots. The tubing and channel may have a pair of inlet and outlet. The inlet and outlet may be at the same end or different ends of the plate. The structures and functions described above regarding the heat exchange plate are not exhaustive and are not limiting; after consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope. For example, in some embodiments, the heat exchange plate does not have any slot.

In some embodiments, the tubing and the plate are made of materials with high thermal conductivity, such as materials having a high heat conduction coefficient, thus heat exchange plate is capable of efficient heat conduction to dissipate heat quickly from a heat source. The fabrication material(s) of the tubing and the plate may be the same or different. Particularly, the tubing and/or the plate may be made of a metallic material, a nonmetallic material, an alloy material or a combination thereof. For example, in some embodiments, the tubing and/or the plate can be made of a non-ferromagnetic material such as copper, aluminum, aluminum alloy, alloy steel, or carbon fiber. In some embodiments, the tubing and/or the plate can be made of a thermal conductive polymer such as epoxy, plastic, silicon, resin and rubber. In some embodiments, the tubing and/or the plate can be made of an organic material. Particularly, in some embodiments, the tubing and/or the plate is made of copper or aluminum. More particularly, in some embodiments, the tubing is made of copper and plate is made aluminum. Fabrication materials described above are not exhaustive and are not limiting. Additional materials suitable for the purpose of the present disclosure, either readily available or to be discovered or made in future, may be ascertained to one skilled in the art, and it is intended that the present disclosure encompass all such materials as falling within the scope of the present disclosure.

In some embodiments, the tubing may be embedded into the heat exchange plate 412 by mechanical pressing or pasting. In some embodiments, connections between the tubing and the heat exchange plate are seamless. In other embodiments, gaps between the tubing and the heat exchange plate can be filled with a thermal conductive material(s). In various embodiments, the thermal conductive material can be metal, non-metal or alloy, such as silicone, oil, air, plastic, resin, gel, other thermal conductive organic or inorganic polymers or any suitable materials currently available in the field or to be discovered or made in future.

In some embodiments, one or more slots can be formed by punching, drilling, milling, laser-cut, forging, 3D printing, or any other suitable methods. In some embodiments, one or more slots can be filled with an electrical insulating material(s). In some embodiments, the electrical insulating material is also thermal conductive. For example, in various embodiments, the electrical insulating material can be silicon, air, plastic, resin, gel, other thermal conductive organic or inorganic polymers or any suitable materials currently available in the field or to be discovered or made in future.

In some embodiments, the tubing and channel are configured to deliver a heat exchange media to the close vicinity of a target component or location within the PET detector module that generates heat during operation. Particularly, in some embodiments, the heat exchange media is a fluid having high thermal capacity. Thus, when the heat exchange media flows through or around the target component or location, it transfers the heat to other locations or dissipates it. In some embodiments, the heat exchange media has low viscosity, is low cost, non-toxic and chemically inert, neither causing nor promoting corrosion of the system. In some embodiments, the heat exchange media is electrical insulating. In some embodiments, the heat exchange media can maintain either liquid or gaseous phase, while in other embodiments, the heat exchange media can undergo phase transition, adding the latent heat to the cooling efficiency. In some embodiments, the heat transferred by the heat exchange media can be utilized by other devices within or external to the imaging system. In some embodiments, the heat exchange media circulates within the system, while in other embodiments heated heat exchange media may be extracted from the system and used for other purposes. In some embodiments, the heat exchange media may be a cooling media. In alternative embodiments, the heat exchange media may be a heating media. The heat exchange media can be in gaseous, liquid or solid state. For example, in various embodiments, the heat exchange media may be air, hydrogen, inert gases, carbon dioxide, sulfur hexafluoride, steam, water, oil, Betaine, deionized water, heavy water, polyalkylene glycol (PAG), cutting fluid, oils such as mineral oils, castor oils, silicone oils, fluorocarbon oils, transformer oil, fuels such as Kerosene and other jet fuels, Freons, refrigerants such as Halomethanes and anhydrous ammonia, liquid gases such as liquified propane, liquified carbon dioxide, or liquid nitrogen, molten metals and salts, or any other heat exchange medium either currently available in the field or to be discovered or made in future. The types of other heat exchange medium described above are not exhaustive and are not limiting. Additional materials suitable for the purpose of the present disclosure, either readily available or to be discovered or made in future, may be ascertained to one skilled in the art, and it is intended that the present disclosure encompass all such materials as falling within the scope of the present disclosure.

In some embodiments, heat exchange media circulates within the PET imaging modality. The heat exchange media is driven to the circulation system 201 by the cooling apparatus 205, passing over the close vicinity of a target component or location within the PET detector module that generates heat during operation, and returning to the cooling apparatus 205 via the outlet 204 of the circulation system 201. Particularly, in some embodiments, the heat exchange media is delivered to the heat exchange plate placed closely to the PET detector module and flows through the heat exchange plate via either the tubing embedded within the plate or the internal channels.

In some embodiments, the heat exchange plate comprises electrical conductive materials, thus may induce eddy effect. The eddy effect on the imaging modalities may relate to the magnitude of the eddy currents. The magnitude of the eddy current in a given loop is proportional to the strength of the magnetic field, the area of the loop, the rate of change of flux, and inversely proportional to the resistivity of the material. The eddy effect induced by the heat exchange plate may be evaluated. Example 1 illustrates an exemplary method may be used to evaluate the eddy effect according to some embodiments of the present disclosure. The heat exchange plate with slots reduce the area perpendicular to the magnetic field of the MR imaging modality, thus reduces the eddy effect that would have been brought. As shown in Example 2, the heat exchange plate with slots shows little impact on the gradient field of the MR imaging modality. As shown in Example 3, the heat exchange plate with slots shows little impact on the homogeneity of the main magnetic field of the MR imaging modality.

Figure 9A:
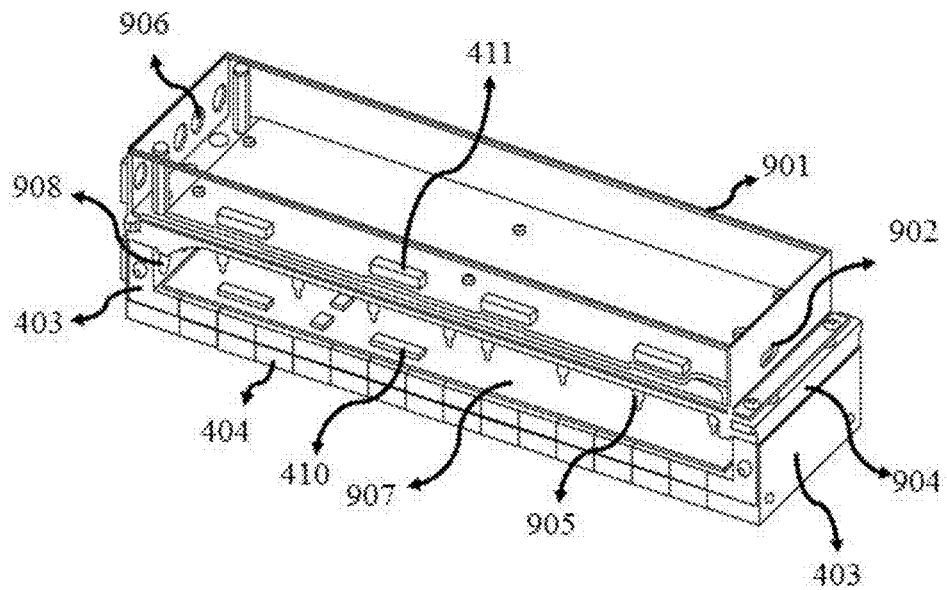
FIGS. 9A and 9B illustrate another specific embodiment of a PET detector module according to some embodiments of the present disclosure. Particularly.
Figure 9B:
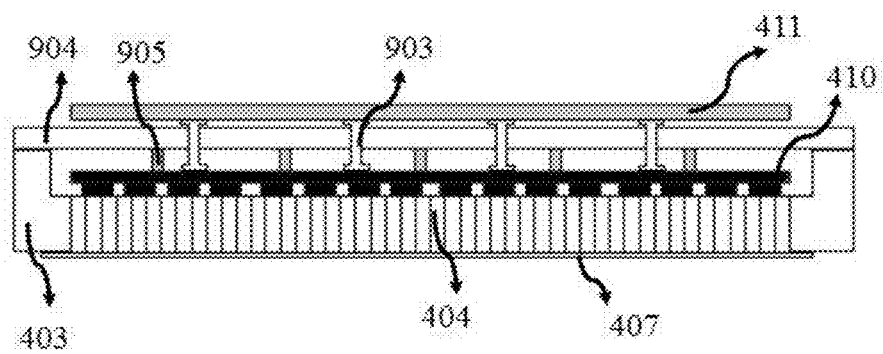

FIGS. 9A and 9B illustrate another specific embodiment of a PET detector module according to some embodiments of the present disclosure. Particularly, FIG. 9A is a schematic drawing illustrating a perspective view of the PET detector module and FIG. 9B is a schematic drawing illustrating a cross-section view of the PET detector module.

As shown in FIG. 9A, the PET detector module comprises a scintillator 404, a set of frontend electronics 410, a set of readout electronics 411, a pair of fixation blocks 403, a supportive frame 904, and a spring mechanism 905. As shown in the figure, each fixation block 403 has a step-like shape. The scintillator 404 comprises an array of scintillator crystals mounted between the lower steps of the fixation blocks 403. The supportive frame 904 is mounted on the higher steps, leaving a cavity 907 between the supportive frame 904 and the scintillator crystal array 404. The cavity 907 has the thickness of fixation block step. The cavity 907 houses the frontend electronics 410 and the spring mechanism 905. The readout electronics 411 are mounted on top of the supportive frame 904, and thus are separated from the frontend electronics 412. Communication between the frontend electronics 410 and readout electronics 411 may be achieved by connecting cables 903. In some embodiments, the PET detector module further comprises data output 902 for transmitting signals to other components of the imaging system, such as the image reconstruction processor 105 or the memory 106 of the system.

As shown in FIG. 9B, the spring mechanism 905 is fixed between the supportive frame 904 and the frontend electronics 410. The spring mechanism 905 comprises a set of springs extending towards the frontend electronics 410. Thus the set of springs 905 exert point pressure upon the frontend electronics against the scintillator crystal array 404, stabilizing the contact and communication between the two. In some embodiments, the point pressure is applied upon individual components of the frontend electronics 410. In other embodiments such as shown in FIG. 9B, the frontend electronics 410 are mounted on one piece of circuit board, and the point pressure of the spring mechanism 905 is applied on the board.

In some embodiments, the PET detector module further comprises a supportive layer 407 to stabilize the scintillator crystal array 404 against the applied pressure. Particularly, as shown in FIG. 9B, the supportive layer 407 connects between the pair of fixation blocks 403, and supports the scintillator crystal array 404 from the surface opposing to where the frontend electronics 410 attach. In some embodiments, the supportive layer 407 is made of a material(s) capable of affording sufficient physical support at a small thickness, and does not block gamma ray at any substantial level. The supportive layer 407 can be made of any suitable materials currently available in the field or to be discovered or made in future. For example, in some embodiments, the supportive layer 407 is made of carbon fiber. In some embodiments, the supportive layer 407 is made of metals of low density. For example, the supportive layer 407 may be made of thin aluminum plate.

In some embodiments, the PET detector module further comprises a temperature control mechanism. More particularly, in some embodiments, the temperature control mechanism is an air-cooling or air-warming system. Particularly, the PET detector module comprises structural elements that form an air passage surrounding a target component or location in the PET detector module. For example, as shown in FIG. 9A, the PET detector module further comprises air passages above and beneath the supportive frame 904. Particularly, an air box 901 is sealed on top the supportive frame 904. The air box 901 has a set of air inlet/outlet 906 at one end. Near the opposing end of the air box 901, the supportive frame 904 has an opening, thus connecting the air box 901 with the cavity 907. The cavity 907 is air sealed except for having a set of air inlet/outlet 908.

As shown in FIG. 9A, in this exemplary embodiment, air inlet/outlet 906 and air inlet/outlet 908 are arranged at the same end of the PET detector module. Thus, in some embodiments, cooling air may flow into the PET detector module through inlet 906. The air then flows through the air box 901, cooling off readout electronics 411. The air then enters the cavity 907 through the opening of the supportive frame 904. The air flows through the cavity, cooling off frontend electronics 410 before exiting the PET detector module through outlet 908. In some embodiments, the direction of airflow may be reversed, and the frontend electronics 410 are cooled off before the readout electronics 411. In some embodiments, hot air may be delivered into the PET detector module to warm up components therein. The structure described above regarding the heat exchange plate is not exhaustive and are not limiting; after consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope. For example, in alternative embodiments, the supportive frame 904 has openings at various locations along its length, creating additional air passages between the space surrounding the frontend and readout electronics (410, 411).

Figure 10:
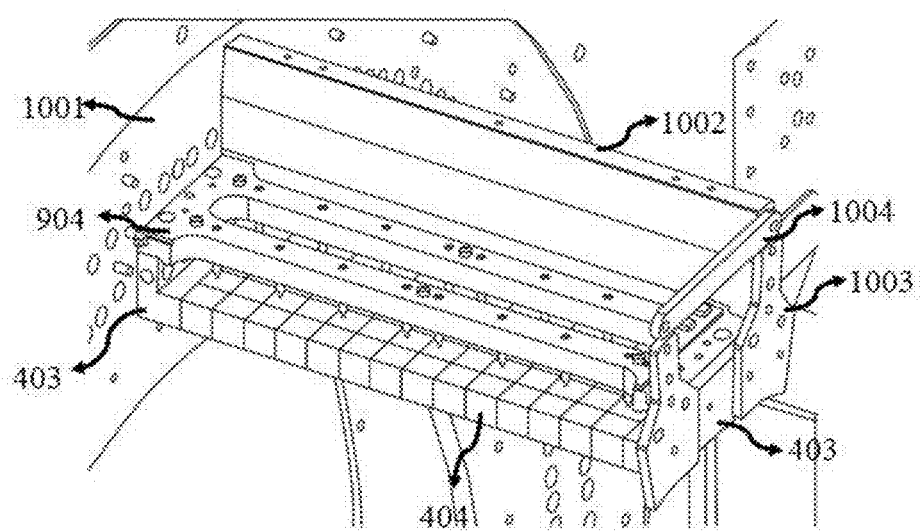
FIG. 10 illustrates exemplary mechanical parts for assembling a PET detector module into a PET detector according to some embodiments of the present disclosure.

According to the present disclosure, a PET detector may comprise multiple PET detector modules assembled together. FIG. 10 illustrates exemplary mechanical parts for assembling a PET detector module into a PET detector according to some embodiments of the present disclosure. As shown in the figure, the mechanical parts comprise a main installation plate 1001, a guide groove 1002, a fixation plate 1003, a stopper 1004, a supportive frame 904, and a pair of fixing blocks 403. In various embodiments, the main installation plate 1001 may assume different shapes, such as a circular ring or a square ring, depending on specific designs of the system. The main installation plate 1001 is equipped with a plurality of mechanical fasteners, such as screws and screw holes. As shown in FIG. 10, the main installation plate 1001 directly connects to one fixation block 403 and one end of the supportive frame 904. The supportive frame 904 is coupled to the pair of fixation blocks 403. Thus, the PET detector module is mechanically secured to the main installation plate 1001. The main installation plate 1001 may further connect to other components to enhance the structure. For example, the guide groove 1002 may also connect to the main installation plate 1001 on one end, and to the fixation plate 1003 and the stopper 1004 on the other end. The guide groove 1002 may further connect to the supportive frame 904 on the side. The stopper 1004 is configured to maintain the distance between the two fixation plates 1003. The fixed distance decreases the possibility of deformation of the scintillator crystal array 404.

It should be noted that the above mechanical linkage among components of the system and the method of linkage are merely exemplary. Numerous other changes, substitutions, variations, alterations, and modifications may be ascertained to one skilled in the art and it is intended that the present disclosure encompass all such changes, substitutions, variations, alterations, and modifications as falling within the scope.

Figure 11:
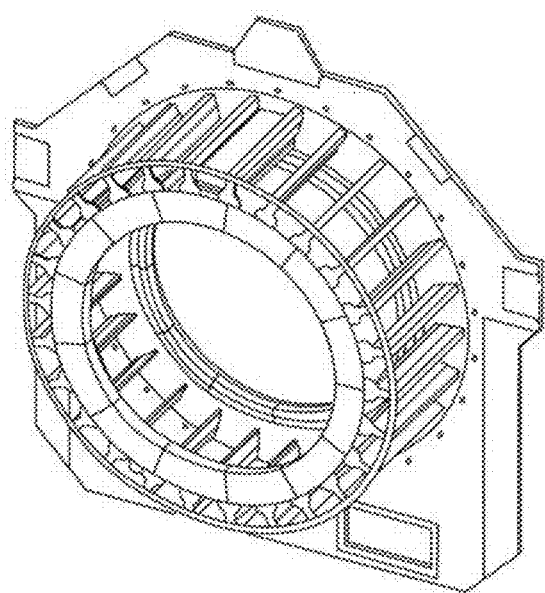
FIG. 11 shows an exemplary barrel-shaped configuration of a PET detector according to some embodiments of the present disclosure.

FIG. 11 shows an exemplary barrel-shaped configuration of a PET detector according to some embodiments of the present disclosure. As shown in the figure, the PET detector comprises a plurality of PET detector modules assembled together. The plurality of PET detector modules may corporately form a scanning bore. The barrel configuration has a hollow space in the center, which is the sample area for holding an imaging target body. The plurality of PET detector modules can be divided into several opposing pairs. Each pair flanks the sample area and has their respective scintillator face opposing one another.

In some embodiments, the PET detector may further comprise a plurality of heat exchange plates. The plurality of heat exchange plate may arrange outward of the detector modules. Each heat exchange plate may comprise a fluidic passage and a plate. The plate may have a first surface and a second surface opposite to the first surface. The plate may further comprise a front end and a rear end opposite to the front end. The first surface and the second surface may respectively extend from the front end to the rear end of the plate. The plate may further comprise a slot. The slot may substantially extend along a direction parallel to an axial direction of the scanning bore. The slot may penetrate the first surface and the second surface, and may be blocked by the front end or the rear end of the plate. The fluidic passage may be associated with the plate.

It should be noted that the PET detector configuration as shown in FIG. 11 is for illustrative purpose only, and not intended to be limiting. According to the present disclosure, a PET detector can have a plurality of detector modules arranged in various different configurations. In some embodiments, a PET detector can have a pair of detector modules flanking a sample area, the scintillator faces of the pair of detector modules opposing one another. In other embodiments, a PET detector can have multiple pairs of detector modules, each pair of detector module flanking the sample area with their scintillator faces opposing one another. The plurality detector modules of a PET detector can form various different configurations. For example, the PET detector modules may be assembled into a unified structure, such as shown in FIG. 11, or may remain structurally separated from one another, such as shown in FIG. 5. In some embodiments, a plurality of PET detector modules may form more than one unified structure. The size of the sample area may be adjusted by assembling the PET detector modules differently. In various embodiments, the adjustment may include changing the distance between each pair of detector blocks, or increasing the number of the detector modules to form a larger barrel.

In various embodiments, the PET detector modules may be assembled onto the patient table or integrated into the imaging gantry of the system. In some embodiments, the assembly may be reversible. For example, one or more PET detector modules may be temporarily removed from the system to accommodate various needs in practice. The above structures and functions regarding the PET detector are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

EXAMPLES

The following examples are for illustrative proposes only and should not be interpreted as limitations of the claimed invention. There are a variety of alternative techniques and procedures available to those of ordinary skill in the art, which would similarly permit one to successfully perform the intended invention.

Example 1

Evaluation of Eddy Effect

FIG. 12A through FIG. 12B illustrate a method of evaluating effect of eddy currents brought by the heat exchanger according to some embodiments of the present disclosure.

FIG. 12A illustrates a method of evaluating the effect of eddy currents on the magnetic fields brought by the heat exchange plate according to some embodiments of the present disclosure. As shown in the figure, a sample 1202 is placed within the imaging gantry 1201 of the MR imaging modality. The sample may be any samples suitable for the evaluation, such as a tissue, an organ, or a man-made material. In some embodiments of the present disclosure, the sample 1202 is a water phantom. The water phantom 1202 is a thin, hollow object filled with water, oil, and/or the like, and/or the combination thereof. The samples that can be used in connection with the present system described herein are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

During the evaluation, the water phantom is placed within the imaging gantry 1201 of the MR imaging modality parallel to the coronal plane, the traverse plane, and the sagittal plane, respectively. Referring to the three-dimensional coordinates x, y and z as shown in the figure, the coronal plane may refer to the plane parallel to the plane defined by the x and z axes. In some embodiments where a human patient is examined on a patient table using the system according to the present disclosure, the coronal plane may separate the front (anterior) from the back (posterior). The traverse plane may refer to the plane parallel to the plane defined by the x and y axes. In some embodiments where a human patient is examined on a patient table using the system according to the present disclosure, the traverse plane may separate the head (superior) from the feet (inferior). The sagittal plane may refer to the plane parallel to the plane defined by the y and z axes. In some embodiments where a human patient is examined on a patient table using the system according to the present disclosure, the sagittal plane may separate the left from right. The coronal plane, traverse plane and sagittal plane are perpendicular to each other. In some embodiments, the magnetic strength of the gradient field may vary along the one of the x, y, z directions.

The evaluation comprises two tests examining the water phantom with and without the heat exchange plate in the system. The first test is performed such that the water phantom is examined without any heat exchange plate in the system. Images of the water phantom along the x, y and z axes are generated at each position of the water phantom and nine images are obtained. The nine images are arranged in a matrix according to FIG. 12B. Images of the water phantom obtained when the water phantom is placed parallel to the coronal plane are arranged in the top row, images of the water phantom obtained when the water phantom is placed parallel to the sagittal plane are arranged in the middle row, and images of the water phantom obtained when the water phantom is placed parallel to the traverse plane are arranged in the bottom row. Images in each row are further arranged in the following order: from left to right, the image along z axis, the image along x axis, and the image along y axis.

The second test is performed such that a heat exchange plate is then installed into the system and the water phantom is examined again in similar manner as described above. In some embodiments, the first test and the second test may be performed sequentially using the same imaging device. In some embodiments, the first test and the second test may be performed simultaneously using different imaging device with the same or substantially the same parameters. Preferably, the first test and the second test are performed in a short time interval using the same imaging device. The images of the water phantom with and without the heat exchange plate in the system are compared to determine the effect of eddy currents brought by the heat exchange plate on the imaging modalities.

During evaluation, the heat exchange plate may be installed in places of the PET/MR hybrid system suitable for the purpose of imaging. Preferably, one or more heat exchange plates are installed where an image of high quality may be achieved in actual imaging, as shown in FIG. 5. In some embodiments, the heat exchange plate may be installed in between the gradient coil of the MR system and the RF coil of the MR system. In some embodiments, the heat exchange plate may be inserted into the patient table. It should be noted that the places that the heat exchangers may be installed described above is provided for the purposes of illustration, and not intended to limit the scope of the present disclosure. Apparently for persons having ordinary skills in the art, numerous variations and modifications may be conducted under the teaching of the present disclosure. However, those variations and modifications may not depart the protecting scope of the present disclosure.

It should be noted that the evaluation method described above is provided for the purposes of illustration, and not intended to limit the scope of the present disclosure. Apparently for persons having ordinary skills in the art, numerous variations and modifications may be conducted under the teaching of the present disclosure. However, those variations and modifications may not depart the protecting scope of the present disclosure.

Example 2

Exemplary Results for the Eddy Effect on the Gradient Magnetic Field

Figure 13A:
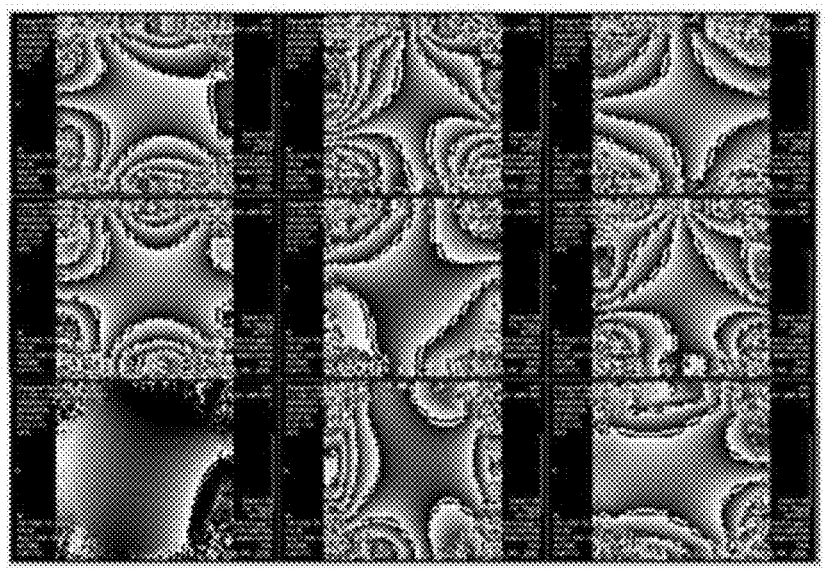
FIGS. 13A and 13B illustrate an exemplary test results for the effect of the heat exchange plate on the imaging modality of the imaging system according to some embodiments of the present disclosure.
Figure 13B:
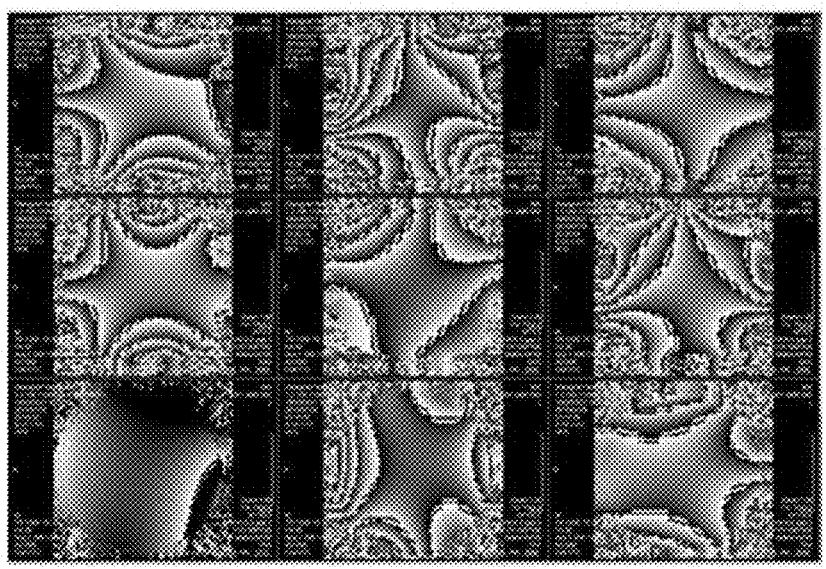

FIGS. 13A and 13B illustrate an exemplary evaluation results of the effect of eddy currents brought by the heat exchange plate according to some embodiments of the present disclosure. FIG. 13A illustrates the image of the sample without the heat exchange plate in the system. FIG. 13B illustrates the image of the sample with a heat exchange plate in the system. In these embodiments, the sample used is a water phantom.

As can be seen in the figures, FIG. 13A and FIG. 13B comprise nine images arranged in a matrix, respectively. The nine images in a matrix are arranged in a way described in FIG. 12B. The images in the same position of the two matrices represent images of the water phantom in the same position along the same axis with and without heat exchangers in the system. For example, the images in the top left corner of the matrix in FIG. 13A and FIG. 13B represent the images of the water phantom placed parallel to the coronal plane along the z axis. As can be seen, the shapes in the two images are substantially the same, the no additional stripes are found in the respective image in FIG. 13B. The result indicates that the eddy effect on the imaging system brought by the present heat exchange plate is minimal or negligible when the sample is imaged in coronal plane along z axis. Similarly, the shapes in the two respective images of the water phantom in the same position along the same axis are all substantially the same, and no additional stripes may be found in the respective image in FIG. 13B. The evaluation indicates that eddy effect on the imaging system brought by the present heat exchange plate is minimal or negligible.

It should be noted that the evaluation results described above is provided for the purposes of illustration, and not intended to limit the scope of the present disclosure. Apparently for persons having ordinary skills in the art, numerous variations and modifications may be conducted under the teaching of the present disclosure. However, those variations and modifications may not depart the protecting scope of the present disclosure.

Example 3

Exemplary Results of the Eddy Effect on the Main Magnetic Field

FIG. 14 illustrates exemplary test results of the effect of the heat exchange plate on the magnetic field according to some embodiments of the present disclosure. Particularly, the table in FIG. 14 illustrates the effect of the heat exchange plate on the main magnetic field, i.e., B0 field, of the MR imaging modality. Different parameters representing the characteristics of the main magnetic field are measured during the tests. First, the parameters are measured without heat exchange plate in the system. Then one or more heat exchange plates are installed into the system and the parameters are measured again. Again, this result indicates that eddy effect on the imagining system brought by the present heat exchange plate is minimal or negligible.

The examples set forth above are provided to give those of ordinary skill in the art a complete disclosure and description of how to make and use the embodiments of the arrangements, devices, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations that is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

What is claimed is:

1. A positron emission tomography (PET) and magnetic resonance (MR) hybrid imaging system comprising a magnetic resonance imaging (MRI) module and a PET module, the MRI module being configured to generate a magnetic field along a direction, the PET module including a heat exchange plate, the heat exchange plate comprising a fluidic passage and a plate, the plate having a cross-section that is perpendicular to the direction of the magnetic field, wherein the fluidic passage is configured to contain a flow of a heat exchange-medium, and the fluidic passage is arranged within a plane that is parallel to the direction of the magnetic field; and wherein the plate comprises at least one slot dividing the cross-section of the plate into a plurality of segments that are electrically insulating to each other.

2. The PET and MR hybrid imaging system of claim 1, wherein the at least one slot each comprises a pair of open and closed ends located at two opposing ends of the plate.

3. The PET and MR hybrid imaging system of claim 2, wherein the open ends of two neighboring slots of the at least one slot are located at the two opposing ends of the plate.

4. The PET and MR hybrid imaging system of claim 2, wherein the open ends of two neighboring slots of the at least one slot are located at a same end of the two opposing ends of the plate.

5. The PET and MR hybrid imaging system of claim 2, wherein the fluidic passage is alongside each of the at least one slot; and wherein the fluidic passage turns 180 degrees around each closed end.

6. The PET and MR hybrid imaging system of claim 1, wherein the at least one slot each comprises a pair of open ends located at two opposing ends of the plate.

7. The PET and MR hybrid imaging system of claim 1, wherein the fluidic passage is a tubing embedded within the plate.

8. The PET and MR hybrid imaging system of claim 1, wherein the fluidic passage is a channel internal to the plate.

9. The PET and MR hybrid imaging system of claim 1, wherein the fluidic passage is a tubing having a first portion, a second portion and a third portion; wherein the first and second portions are embedded within the plate, the first and second portions being alongside the at least one slot;

wherein the third portion is external to the plate, the third portion connecting the first and second portions into fluidic communication.

10. The PET and MR hybrid imaging system of claim 1, wherein the plate is made of an electrically conductive material; and wherein the at least one slot is filled with an electrically insulating material.

11. The PET and MR hybrid imaging system of claim 1, the PET module further comprising a scintillator, a set of frontend electronics, and a positioning means configured to secure a relative position between the scintillator and the set of frontend electronics.

12. The PET and MR hybrid imaging system of claim 11, wherein the positioning means is configured to exert a compressive force that presses the set of frontend electronics against the scintillator, wherein the positioning means comprises a compressive layer having a compressive surface; wherein the compressive layer extends the compressive surface towards the set of frontend electronics; and wherein the compressive surface presses the set of frontend electronics against the scintillator.

13. The PET and MR hybrid imaging system of claim 12, wherein the set of frontend electronics has a first area, wherein the compressive surface has a second area; and wherein the first area and the second area are substantially the same.

14. The PET and MR hybrid imaging system of claim 12, wherein the set of frontend electronics has a first area, wherein the compressive surface has a second area; and wherein the first area is substantially larger than the second area.

15. The PET and MR hybrid imaging system of claim 1, wherein at least one of the at least one slot is parallel to the direction of the magnetic field.

16. The PET and MR hybrid imaging system of claim 1, wherein the plate is made of at least one of a metallic material, a nonmetallic material, or an alloy.

17. The PET and MR hybrid imaging system of claim 1, wherein the plate is 2 to 20 millimeters thick.

18. The PET and MR hybrid imaging system of claim 11, wherein the positioning means includes a first thermally conductive layer placed between the plate and the frontend electronics.

19. The PET and MR hybrid imaging system of claim 18, wherein the PET module further comprises a set of readout electronics and a second thermally conductive layer placed between the plate and the readout electronics.

20. The PET and MR hybrid imaging system of claim 1, wherein the PET module further comprises:
 a scintillator;
 a set of frontend electronics;
 a set of readout electronics;
 a pair of step-like shape fixation blocks each having a lower step and a higher step; and
 a supportive frame mounted on the higher steps of the pair of fixation blocks;
 wherein,
 the scintillator is mounted between the lower steps of the pair of fixation blocks;
 the set of readout electronics are mounted on top of the supportive frame; and
 the set of frontend electronics are housed between the scintillator and the supportive frame.

* * * * *